US007706060B2

(12) United States Patent
Mogami et al.

(10) Patent No.: US 7,706,060 B2
(45) Date of Patent: Apr. 27, 2010

(54) MICROSCOPIC CELL OBSERVATION AND INSPECTION SYSTEM USING A PLURALITY OF OBSERVATION METHODS

(75) Inventors: Hideo Mogami, Hamamatsu (JP); Yohei Sato, Yokohama (JP); Yutaka Kazoe, Yokohama (JP)

(73) Assignees: National University Corporation Hamamatsu University School of Medicine, Hamamatsu-Shi (JP); Keio University, Tokyo (JP)

( * ) Notice: Subject to any disclaimer, the term of this patent is extended or adjusted under 35 U.S.C. 154(b) by 0 days.

(21) Appl. No.: 11/992,549
(22) PCT Filed: Sep. 13, 2006
(86) PCT No.: PCT/JP2006/318546
§ 371 (c)(1),
(2), (4) Date: Mar. 25, 2008
(87) PCT Pub. No.: WO2007/034796
PCT Pub. Date: Mar. 29, 2007

(65) Prior Publication Data
US 2009/0052021 A1    Feb. 26, 2009

(30) Foreign Application Priority Data
Sep. 26, 2005    (JP)    ............................. 2005-277501

(51) Int. Cl.
*G02B 21/06*    (2006.01)
(52) U.S. Cl. .................. 359/388; 359/393; 359/390; 359/385
(58) Field of Classification Search ................ 359/385, 359/390, 391, 393, 388
See application file for complete search history.

(56) References Cited
U.S. PATENT DOCUMENTS 4,297,032 A  * 10/1981 Temple ..................... 356/366
5,249,077 A  *  9/1993 Laronga et al. ............ 359/385
5,780,857 A  *  7/1998 Harju et al. ................ 250/458.1
5,982,534 A  * 11/1999 Pinkel et al. ............... 359/387
6,790,632 B2 *  9/2004 Zweig ....................... 435/7.92

(Continued)

FOREIGN PATENT DOCUMENTS
DE    10 2004 012 257 A1    10/2004

(Continued)

OTHER PUBLICATIONS

P.B. Conibear, et al.; "A comparison of optical geometries for combined flash photolysis and total internal reflection fluorescence microscopy;" *Journal of Microscopy*; vol. 200; Pt. 3; Dec. 2000; pp. 218-229 and one sheet of advertising (13 Sheets total.).

(Continued)

*Primary Examiner*—Alessandro Amari
*Assistant Examiner*—Mark Consilvio
(74) *Attorney, Agent, or Firm*—Kratz, Quintos & Hanson, LLP

(57) ABSTRACT

The invention relates to a microscopic cell observation and inspection system that uses a total internal reflection cell illuminator that is capable of freely changing an observation position without recourse to any special slide glass, makes sure high SN-ratio observation and facilitates sample manipulation, thereby making high-sensitivity, fast detection of a lot of cell reactions on the same slide glass. While, in response to a command from personal computer (80), step motors (53, 54) are driven to sequentially scan observation positions of cell sample (S) on slide glass (21), one of shutter units (71) and (72) is closed and the other is opened at high speed, whereby either one of illumination optical paths for a TIRF microscope and a drop fluorescence microscope is selected to illuminate cell sample (S) on that observation position. When the drop fluorescence microscope is chosen, filter unit (66) is driven to choose the wavelength of excitation light from drop fluorescence illumination light source (65), so that observation and inspection of cell sample (S) under the TIRF microscope and drop fluorescence microscope can be implemented in an alternate fast switchover way.

6 Claims, 15 Drawing Sheets

U.S. PATENT DOCUMENTS

| | | |
|---|---|---|
| 6,924,930 B2 * | 8/2005 | Uhl .......................... 359/389 |
| 7,369,308 B2 * | 5/2008 | Tsuruta et al. ............. 359/388 |
| 2003/0155527 A1 | 8/2003 | Natori |
| 2004/0196549 A1 | 10/2004 | Aono |
| 2005/0179903 A1 * | 8/2005 | Tsuruta et al. ............. 356/445 |
| 2005/0207005 A1 * | 9/2005 | Kawano ..................... 359/388 |
| 2006/0257886 A1 * | 11/2006 | Kobayashi et al. ............ 435/6 |
| 2006/0280404 A1 * | 12/2006 | Kennedy et al. ............. 385/31 |
| 2007/0097496 A1 * | 5/2007 | Ulrich et al. ................ 359/385 |
| 2007/0109536 A1 * | 5/2007 | Weiss et al. ................. 356/318 |
| 2007/0159690 A1 * | 7/2007 | Ulrich et al. ................ 359/385 |
| 2007/0177258 A1 * | 8/2007 | Eijsackers et al. ........... 359/393 |
| 2008/0179491 A1 * | 7/2008 | Karasawa et al. ........ 250/201.2 |

FOREIGN PATENT DOCUMENTS

| | | |
|---|---|---|
| JP | 11211990 A * | 8/1999 |
| JP | 2003-270524 | 9/2003 |
| JP | 2003-270538 | 9/2003 |
| JP | 2004-295122 | 10/2004 |

OTHER PUBLICATIONS

M.N. Teruel, et al.; "Parallel Single-Cell Monitoring of Receptor-Triggered Membrane Translocation of a Calcium-Sensing Protein Module;" *Science*; vol. 295; Mar. 8, 2002; pp. 1910-1912 and one sheet of Table of Contents (4 Sheets total.).

* cited by examiner

FIG. 6
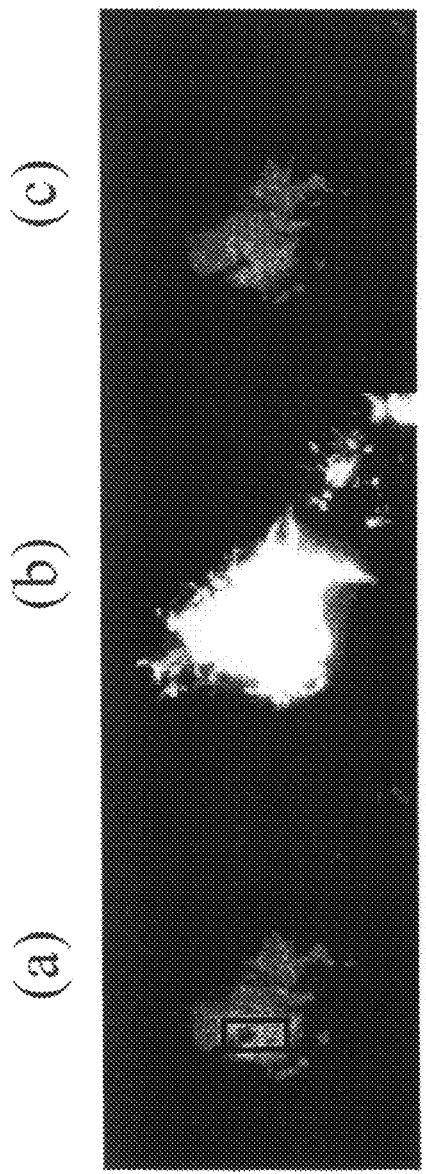
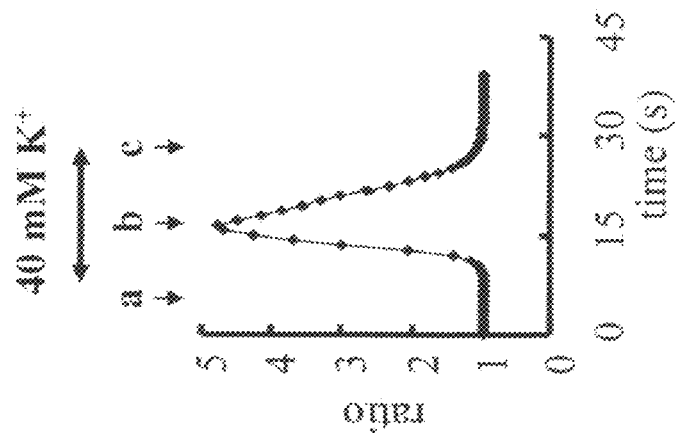

FIG. 14
(a) (Prior Art)
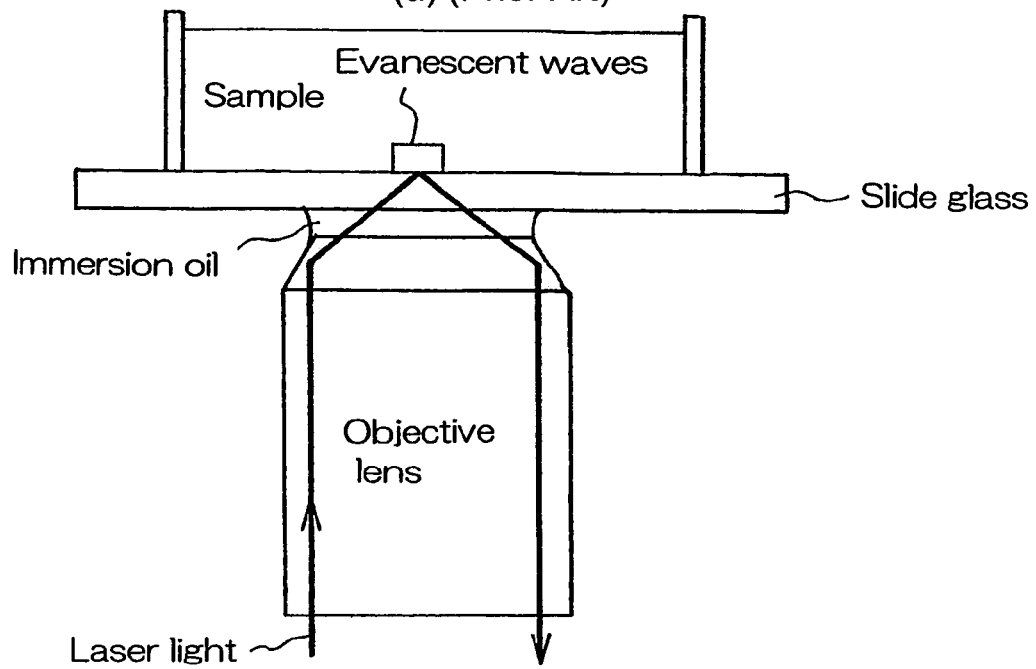
(b) (Prior Art)
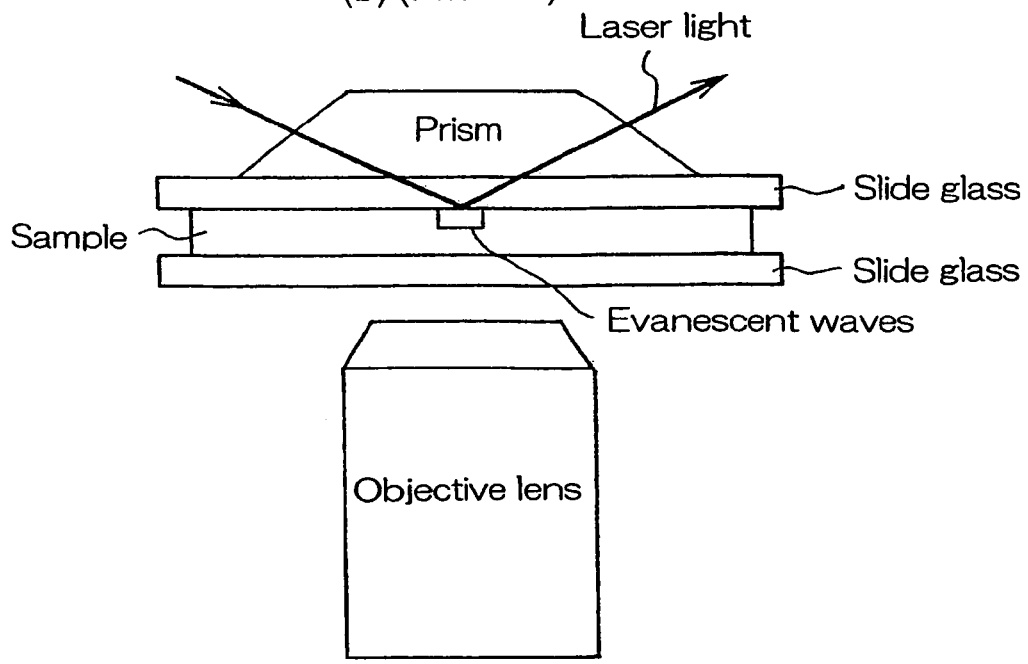

FIG. 15
(a) (Prior Art)
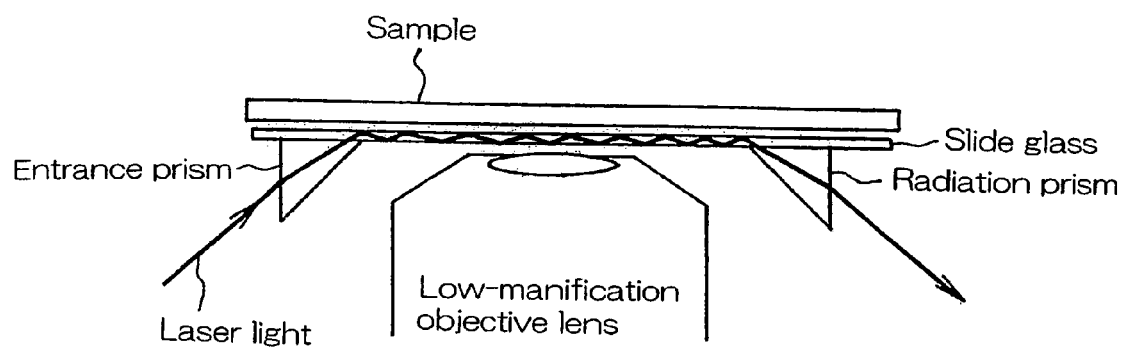
(b) (Prior Art)
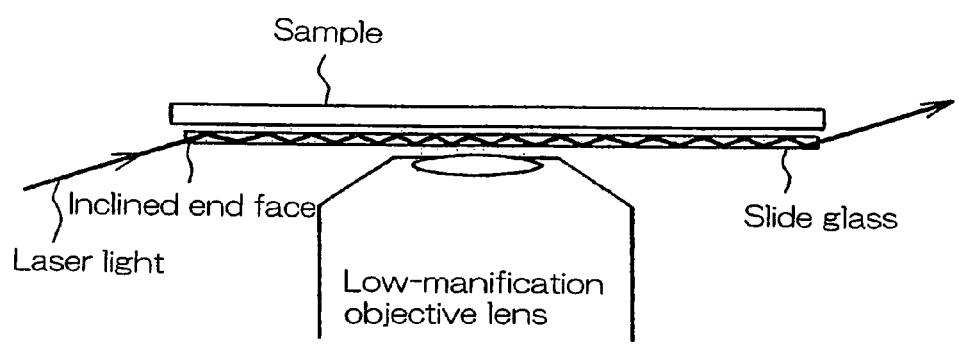

MICROSCOPIC CELL OBSERVATION AND INSPECTION SYSTEM USING A PLURALITY OF OBSERVATION METHODS

ART FIELD

The present invention relates generally to a microscopic cell observation and inspection system using a plurality of observation methods, and more particularly to a microscopic cell observation and inspection system that can combine a total internal reflection fluorescence (TIRF for short) microscope with other microscopes based on optical observation methods such as a confocal fluorescence microscope for fast, high-sensitivity detection of as many as several hundreds of cell reactions on the same slide glass, and can be incorporated into drug design screening apparatus.

BACKGROUND ART

The TIRF microscope technique is a high SN-ratio observation method capable of local excitation on nano-scales. This technique has been widely used for observation of cell membrane activities and single-molecule events in the cell biological field (see Non-Patent Publication 1), and it has made much contributions to experimental revelation of the electrical properties (Non-Patent Publication 1) or Brownian movement of colloidal particles in the electrochemical field as well (Kihm, K. D. et al., Exp. in Fluids, 37, pp. 811-824, (2004). The most noticeable feature of this method is that for fluorescent observation, there are evanescent waves used as an excitation light source, which are generated in association with total internal reflection at an interface of two substances having different refractive indexes. FIG. 1 is illustrative of how the evanescent waves are generated; when, on the interface of a substance 1 having a refractive index $n_1$ and a substance 2 having a refractive index $n_2$, light is incident from the side of the substance 2 having a higher refractive index at an angle larger than the critical angle, the light is subjected to total internal reflection at that interface. However, there are some evanescent waves unavoidably generated from the interface to the side of the substance 1 having a lower refractive index, which waves attenuate exponentially. The evanescent waves are light showing up slightly from the total internal reflection interface to an area of about a few tens to a few hundred nm. In the TIRF technique, therefore, evanescent waves are generated at an interface of a sample stained with fluorescent dye and a slide or cover glass (hereinafter called the slide glass) to enable high SN-ratio fluorescent observation at only a limited sample site.

What is now commercially available and generally often used is mainly such an objective lens type TIRF microscope as shown in FIG. 14 (a). More specifically, an objective lens of the inverted type is positioned below the slide glass via an oil-immersion oil, and evanescent wave-generation laser light is obliquely incident from below the slide glass via that objective lens so that evanescent waves are generated near the interface with a sample placed on the slide glass. This arrangement performs well and is convenient because the space above the objective lens is freely accessible, and it gives a very bright fluorescent image as well. However, the principal requirement for use of a high-aperture, oil immersion objective lens is supposed to limit observation to one at magnifications of as high as 60 or greater.

A prism type TIRF microscope adapted to enter laser via a prism such as the one shown in FIG. 14(b) has been widely used, too. In this case, a sample is held between two slide glasses with the prism placed on one side glass, and evanescent wave-generation laser light is entered obliquely up in the upper slide glass to generate evanescent waves near the interface of the slide glass in contact with the sample. This arrangement is capable of high SN-ratio observation because of efficient incidence of laser light, and enables low-magnification observation to be easily implemented because of no restriction on magnification at all. However, the space above the objective lens is closed up, resulting in very poor specimen manipulation and more limited degrees of sample flexibility.

As described above, the TIRF microscopes are still far away from meeting the need of making simultaneous comparisons at a plurality of samples of reactions that cells exhibit to various chemicals applied in the process of experimentation. Thus, there is a mounting demand for the development of a TIRF microscope that makes sure good enough specimen manipulation and sample flexibility, facilitates combined use with other optical observation methods, and enables observation at low magnifications.

Past studies include Non-Patent Publication (3) wherein, as shown in FIG. 15(a), an entrance prism and a radiation prism are bonded to the underside of a slide glass; laser light is introduced from the entrance prism into the slide glass where it is subjected to multiple total internal reflection; during that multiple total internal reflection, evanescent waves are generated near the upper surface of the slide glass to excite a specimen; and the laser light guided by multiple total internal reflection goes out via the radiation prism, and Non-Patent Publication 4 wherein, as shown in FIG. 15(b), an end face of a slide glass is processed into an inclined one; laser light is introduced from that inclined end face into the slide glass to subject it to multiple total internal reflection; and upon that multiple total internal reflection, evanescent waves are generated near the upper surface of the slide glass to excite a specimen; and the laser light guided by multiple total internal reflection goes out from the opposite end face of the slide glass. These methods take hold of a free space above the sample and facilitates low-magnification observation, but because the slide glass is limited to a small thickness (0.17 mm in the former, and 0.2 mm in the latter), they offer some problems: a lot more multiple total internal reflections, the occurrence of scattered light due to total internal reflection, attenuation of guided light, the likeliness of the specimen to discolor due to fluorescence, and lower SN ratios. Further, the positions of incidence and radiation of laser light remain fixed, rendering it hard to adjust an optical path for laser light, and making sample manipulation not easy because of the need of moving the objective lens to change a specimen observation position. Yet further, much work is needed with decreased versatility, because of the need of bonding the prisms to the slide glass for each sample.

Non-Patent Publication 1
Axelrod, D., Traffic, Vol. 2, pp. 764-774, (2001)
Non-Patent Publication 2
Prieve, D. C, and Frej. N. A., Langmuir, 6, pp. 396-403, (1990)
Non-Patent Publication 3
Conibear, P. B. and Bagshaw, C. R., Journal of Microscopy, Vol. 200, Pt 3, pp. 218-229, (2000)
Non-Patent Publication 4
Teruel, M. N, and Meyer, T., Science, Vol. 295, pp. 1910-1912, (2002)

SUMMARY OF THE INVENTION

In view of such problems with the prior art, the invention has for its object the provision of a microscopic cell observation and inspection system using a plurality of observation methods, which uses a total internal reflection illuminator that enables an observation position to be freely changed on any slide glass without recourse to any special one, makes sure high SN-ratio observation with much more reduced scattered light and facilitates specimen manipulation to make high-sensitivity, fast detection of as many as several hundreds or more of cell reactions on the same slide glass.

According to one aspect of the invention, the aforesaid object is achievable by the provision of a microscopic observation and inspection system using a plurality of observation methods, characterized by comprising a total internal reflection sample illuminator comprising an evanescent wave-generation light source in which laser light from that light source is introduced into a slide glass through which the laser light is guided by multiple total internal reflections to generate evanescent waves on an upper surface of said slide glass so that a cell sample placed on the upper surface of said slide glass is illuminated with said evanescent waves, wherein:

there is a slide glass position adjustment mechanism located, which adjusts a position of said slide glass in a two-dimensional direction along that surface, a microscope objective lens is located at a position where said slide glass in said total internal reflection sample illuminator is supposed to be placed thereon and in a vertical direction to said slide glass, on an imaging side of said microscope objective lens, an imaging optical system and an imaging device are located in one optical path via an optical path splitter and an excitation light source for a drop fluorescence microscope is located in another optical path, shutter units adapted to block off or transmit illumination light are located, one in an optical path from said evanescent wave-generation light source to a laser light inlet of said slide glass, and another between said excitation light source for a drop fluorescence microscope and said optical path splitter, there is a controller provided which controls an illumination light source switchover by opening or closing each of said shutter units and slide glass position adjustment by said slide glass position adjustment mechanism, and in response to a command from said controller, said slide glass position adjustment mechanism is controlled to select an observation and inspection position for the cell sample on said slide glass, and in response to a command from said controller, the opening or closing of each of said shutter units is controlled so that an illumination light optical path for said evanescent wave-generation light source and an illumination light optical path for said excitation light source for a drop fluorescence microscope are selectively opened, a total internal reflection fluorescence microscope image and a drop fluorescence microscope image at the selected cell sample observation and inspection site on said slide glass are captured in said controller via said imaging device, and cell reactions are detected from said total internal reflection fluorescence microscope image and said drop fluorescence microscope image.

According to another aspect of the invention, there is provided a microscopic observation and inspection system using a plurality of observation methods, characterized by comprising a total internal reflection sample illuminator comprising an evanescent wave-generation light source in which laser light from that light source is introduced into a slide glass through which the laser light is guided by multiple total internal reflections to generate evanescent waves on an upper surface of said slide glass so that a cell sample placed on the upper surface of said slide glass is illuminated with said evanescent waves, wherein:

said total internal reflection sample illuminator comprises an entrance prism and a radiation prism which support said slide glass movably in a plane thereof via a droplet of index-matching liquid, said entrance prism is fixed with respect to said light source, and said radiation prism is located in such a way as to be adjustable in terms of position in a direction of travel of said laser light with respect to said entrance prism, a supporting surface of said entrance prism for said slide glass is flush with a supporting surface of said radiation prism for said slide glass irrespective of a position of the said radiation prism being adjusted, there is a slide glass position adjustment mechanism provided which takes a grip on said slide glass supported on said entrance prism and said radiation prism to adjust a position of said slide glass in a two-dimensional direction along a plane thereof, said total internal reflection sample illuminator is set up such that said laser light leaves said supporting surface via said entrance prism and enters said slide glass supported thereon via said index-matching liquid trickling down thereon through which said laser light is guided by multiple total internal reflection, entering from said supporting surface of said radiation prism into said radiation prism via said index-matching liquid trickling down on said supporting surface of said radiation prism, and is radiated out from said radiation prism, a microscope objective lens is located at a position where said slide glass in said total internal reflection sample illuminator is supposed to be placed between said entrance prism and said radiation prism and in a vertical direction to said slide glass, on an imaging side of said microscope objective lens, an imaging optical system and an imaging device are located in one optical path via an optical path splitter and an excitation light source for a drop fluorescence microscope is located in another optical path, shutter units adapted to block off or transmit illumination light are located, one in an optical path from said evanescent wave-generation light source to a laser light inlet of said slide glass, and another between said excitation light source for a drop fluorescence microscope and said optical path splitter, there is a controller provided which controls an illumination light source switchover by opening or closing each of said shutter units and slide glass position adjustment by said slide glass position adjustment mechanism, and in response to a command from said controller, said slide glass position adjustment mechanism is controlled to select an observation and inspection position for the cell sample on said slide glass, and in response to a command from said controller, the opening or closing of each of said shutter units is controlled so that an illumination light optical path for said evanescent wave-generation light source and an illumination light optical path for said excitation light source for a drop fluorescence microscope are selectively opened, a total internal reflection fluorescence microscope image and a drop fluorescence microscope image at the selected cell sample observation and inspection site on said slide glass are captured in said controller via said imaging device, and cell reactions are detected from said total internal reflection fluorescence microscope image and said drop fluorescence microscope image.

In a preferable embodiment of the invention, said optical path splitter comprises a dichroic mirror and is operable to prevent light having a wavelength of illumination light from said evanescent wave-generation light source and light having a wavelength of illumination light from said excitation light source for a drop fluorescence microscope from arriving at said optical path on the imaging device side but allow only fluorescence emanating from the cell sample to arrive at said optical path on the imaging device side.

In a preferable embodiment of the invention, between said excitation light source for a drop fluorescence microscope and said optical path splitter there is a filter unit located which selects an excitation wavelength, and in response to a command from said controller an excitation wavelength transmitting through said filter unit is selected.

According to yet another aspect of the invention, there is provided a microscopic observation and inspection system using a plurality of observation methods, characterized by comprising a total internal reflection sample illuminator comprising an evanescent wave-generation light source in which laser light from that light source is introduced into a slide glass through which the laser light is guided by multiple total internal reflections to generate evanescent waves on an upper surface of said slide glass so that a cell sample placed on the upper surface of said slide glass is illuminated with said evanescent waves, wherein:

there is a slide glass position adjustment mechanism located, which adjusts a position of said slide glass in a two-dimensional direction along that surface, a microscope objective lens is located at a position where said slide glass in said total internal reflection sample illuminator is supposed to be placed thereon and in a vertical direction to said slide glass, on an imaging side of said microscope objective lens, a filter for blocking off light having a wavelength of illumination light from said evanescent wave-generation light source, a first imaging optical system and a first imaging device are located in one optical path via an optical path splitter, and a confocal scanner for a confocal fluorescence microscope is located in another optical path, on an illumination side of said confocal scanner an excitation light source for the confocal fluorescence microscope is located, and on an output side of said con-focal scanner a second imaging system and a second imaging device are located, shutter units adapted to block off or transmit illumination light or fluorescent light are located, one in an optical path from said evanescent wave-generation light source to a laser light inlet of said slide glass, another in an optical path between said confocal scanner and said optical path splitter, and yet another in an optical path between said optical path splitter and said first imaging device, there is a controller provided which controls an illumination light source switchover by opening or closing each of said shutter units, slide glass position adjustment by said slide glass position adjustment mechanism, and a focus adjustment mechanism adapted to adjust a position of said microscope objective lens in an optical axis direction, and in response to a command from said controller, said slide glass position adjustment mechanism is controlled to select an observation and inspection position for the cell sample on said slide glass, and in response to a command from said controller, the opening or closing of each of said shutter units is controlled so that an illumination light optical path for said evanescent wave-generation light source and an illumination light optical path for a confocal scanner for said drop fluorescence microscope are selectively opened, and when the illumination optical path for the confocal scanner for said confocal fluorescence microscope is opened, said focus adjustment mechanism is controlled to adjust a position of said microscope objective lens in an optical axis direction to a plurality of given positions, whereby a total internal reflection fluorescence microscope image and a confocal fluorescence microscope image at the selected cell sample observation and inspection position on said slide glass are captured in said controller vial said first imaging device and said second imaging device, respectively, so that cell reactions are detected from said total internal reflection fluorescence microscope image and said confocal fluorescence microscope image.

According to a further aspect of the invention, there is provided a microscopic observation and inspection system using a plurality of observation methods, characterized by comprising a total internal reflection sample illuminator comprising an evanescent wave-generation light source in which laser light from that light source is introduced into a slide glass through which the laser light is guided by multiple total internal reflections to generate evanescent waves on an upper surface of said slide glass so that a cell sample placed on the upper surface of said slide glass is illuminated with said evanescent waves, wherein:

said total internal reflection sample illuminator comprises an entrance prism and a radiation prism which support said slide glass movably in a plane thereof via a droplet of index-matching liquid, said entrance prism is fixed with respect to said light source, and said radiation prism is located in such a way as to be adjustable in terms of position in a direction of travel of said laser light with respect to said entrance prism, a supporting surface of said entrance prism for said slide glass is flush with a supporting surface of said radiation prism for said slide glass irrespective of a position of the said radiation prism being adjusted, there is a slide glass position adjustment mechanism provided which takes a grip on said slide glass supported on said entrance prism and said radiation prism to adjust a position of said slide glass in a two-dimensional direction along a plane thereof, said total internal reflection sample illuminator is set up such that said laser light leaves said supporting surface via said entrance prism and enters said slide glass supported thereon via said index-matching liquid trickling down thereon through which said laser light is guided by multiple total internal reflections, entering from said supporting surface of said radiation prism into said radiation prism via said index-matching liquid trickling down on said supporting surface of said radiation prism, and is radiated out from said radiation prism, a microscope objective lens is located at a position where said slide glass in said total internal reflection sample illuminator is supposed to be placed between said entrance prism and said radiation prism and in a vertical direction to said slide glass, on an imaging side of said microscope objective lens, a filter for blocking off light having a wavelength of illumination light from said evanescent wave-generation light source, a first imaging optical system and a first imaging device are located in one optical path via an optical path splitter, and a confocal scanner for a confocal fluorescence microscope is located in another optical path, on an illumination side of said confocal scanner an excitation light source for the confocal fluorescence microscope is located, and on an output side of said con-focal scanner a second imaging system and a second imaging device are located, shutter units adapted to block off or transmit illumination light or fluorescent light are located, one in an optical path from said evanescent wave-generation light source to said entrance prism, another in an optical path between said confocal scanner and said optical path splitter, and yet another in an optical path between said optical path splitter and said first imaging device, there is a controller provided which controls an illumination light source switchover by opening or closing each of said shutter units, slide glass position adjustment by said slide glass position adjustment mechanism, and a focus adjustment mechanism adapted to a position of said microscope objective lens in an optical axis direction, and in response to a command from said controller, said slide glass position adjustment mechanism is controlled to select an observation and inspection position for the cell sample on said slide glass, and in response to a command from said controller, the opening or closing of each of said shutter units is controlled so that an illumination light optical path for said evanescent wave-generation light source and an illumination light optical path for a confocal scanner for said drop fluorescence microscope are selectively opened, and when the illumination optical path for the confocal scanner for said confocal fluorescence microscope is opened, said focus adjustment mechanism is controlled to adjust a position of said microscope objective lens in an optical axis direction to a plurality of given positions, whereby a total internal reflection fluorescence microscope image and a confocal fluorescence microscope image at the selected cell sample observation and inspection position on said slide glass are captured in said controller vial said first imaging device and said second imaging device, respectively, so that cell reactions are detected from said total internal reflection fluorescence microscope image and said confocal fluorescence microscope image.

According to the invention, the total internal reflection sample illuminator is set up such that an observation position on any slide glass can be freely changed without recourse to any special one, high SN-ratio observation is enabled with much more reduced scattered light and sample manipulation is facilitated; it is possible to make high-sensitivity, fast observation and inspection of as many as several hundreds or more of cell reactions on the same slide glass using a plurality of observation methods such as a drop fluorescence microscope technique and a confocal fluorescence microscope technique, and make a lot of contributions to drug design screening, and so on.

BRIEF DESCRIPTION OF THE DRAWINGS

FIG. 6 is illustrative of one example of experimentation about changes in the TIRF microscope image, corresponding to the upper and lower drawings of FIG. 4.

FIG. 14 is illustrative of the principles of how evanescent waves are generated with a commercial objective lens type TIRF microscope and a commercial prism type TIRF microscope.

FIG. 15 is illustrative of how evanescent waves are generated by multiple total internal reflections in a slide glass, as proposed so far.

BEST MODE FOR CARRYING OUT THE INVENTION

Figure 1:
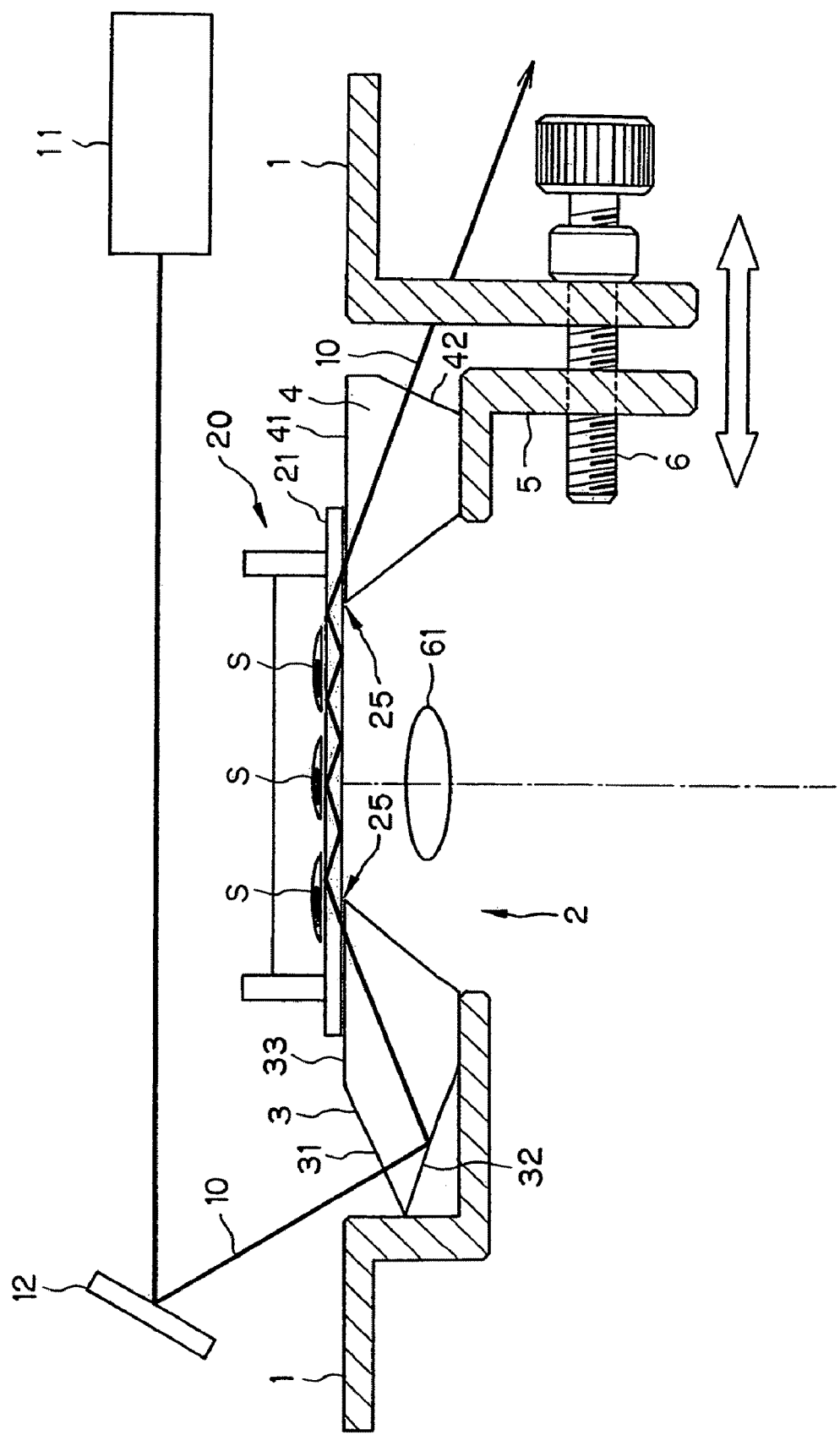
FIG. 1 is illustrative in vertical section of one example of the total internal reflection sample illuminator used with the inventive microscopic cell observation and inspection system.
Figure 2:
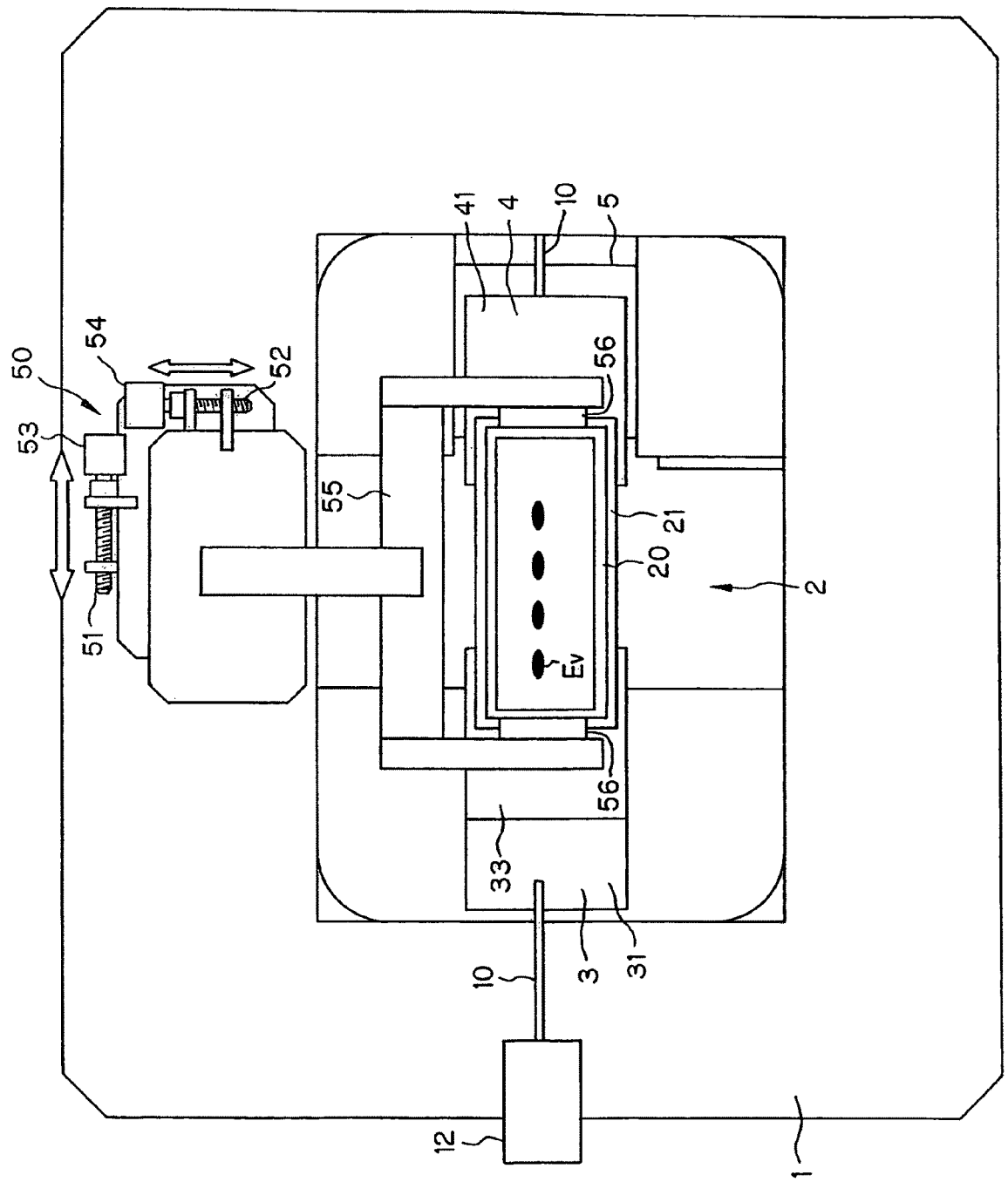
FIG. 2 is illustrative in plan of the total internal reflection sample illuminator of FIG. 1.

The microscopic cell observation and inspection system using a plurality of observation methods according to the invention is now explained with some embodiment and examples. Before that, the total internal reflection sample illuminator—the most important part of the microscopic cell observation and inspection system of the invention—is explained with reference to its example. FIG. 1 is a vertical sectional view of one example of the total internal reflection sample illuminator used with the microscopic cell observation and inspection system according to the invention and FIG. 2 is a plan view of that. This total internal reflection sample illuminator comprises a sample table 1 with an opening 2 provided in its center. Facing the opening 2, an entrance prism 3 is fixed to the sample table 1. Facing the entrance prism 3, a radiation prism 4 is attached to a moving table 5 with the opening 2 held between them such that the space between the radiation prism 4 and the entrance prism 3 is adjustable. This moving table 5 is movable and adjustable by a position adjustment screw 6 toward the entrance prism 3 with respect to the sample table 1. And the entrance prism 3 and the radiation prism 4 are configured and the moving table 5 has a moving mechanism set up such that irrespective of where the moving table 5 is positioned, the transmissive surface 33 of the entrance prism 3 is flush with the transmissive surface 41 of the radiation prism 4.

And a slide glass for supporting a cell sample S, for which a slide glass chamber 20 is here used, is freely placed over the transmissive surface 33 of the entrance prism 3 and the transmissive surface 41 of the radiation prism 4 via an immersion oil 25 trickling down to the transmissive surfaces 33 and 41.

The entrance prism 3 here has a reflection prism configuration comprising a transmissive surface 31 through which evanescent wave-generation laser light 10 is entered from a laser 11 via a reflecting mirror 12, a reflective surface 32 adapted to reflect the incident laser light 10, and a transmissive surface 33 through which the laser light 10 reflected off at the reflective surface 32 goes out, and the radiation prism 4 has a transmission prism configuration comprising a transmissive surface 41 adapted to guide to the outside of the slide glass 21 laser light 10 guided by multiple total internal reflections through the slide glass 21 at the bottom of the slide glass chamber 20, and a transmissive surface 42 adapted to allow the laser light 10 incident from the transmissive surface 41 to radiate out.

The sample table 1 is also provided on its upper surface with a slide glass grip mechanism 55 via an X-Y stage 50. In the example here, the slide glass grip mechanism 55 supports the slide glass chamber 20 by means of elasticity acting in the direction that it is sandwiched between pads 56; by an X-direction position adjustment screw 51 at the X-Y stage 50, the slide glass chamber 20 is movable and adjustable in the X-direction parallel with the incidence direction of the laser light 10; and by a Y-direction position adjustment screw 52 at the X-Y stage 50, the slide glass chamber 20 is movable and adjustable in the Y-direction at right angles with the incidence direction of the laser light 10. And the rotation of the X-direction position adjustment screw 51, and the Y-direction position adjustment screw 52 is controlled by a step motor 53, and 54 to only a given amount, respectively.

The arrangement being like such, even when the slide glass chamber 20 or slide glass 21 placed over the transmissive surfaces 33 and 41 of the entrance prism 3 and radiation prism 4 via the immersion oil 25 is replaced by a different or standard type, there is no need of adjusting the entrance position of the evanescent wave-generation laser light 10 whatsoever, and there is no need of adjusting the position of the laser 11, either, that provides a light source for it. Note, however, that a different thickness of the slide glass 21 causes a change in the reflection position at the bottom surface of the slide glass 21. If, in this case, the position adjustment screw 6 is adjusted to move the moving table 5 in the X-direction, it is then possible to optimize the position of the radiation prism 4 thereby preventing scattered light from occurring.

And the step motors 53 and 54 are rotated a given amount to adjust the X- and Y-direction position adjustment screws 51 and 52 at the X-Y stage 50 to move the slide glass grip mechanism 55 arbitrarily within the plane defined by the transmissive surfaces 33 and 41 of the entrance prism 3 and radiation prism 4 so that the position of the slide glass chamber 20 in that plane is arbitrarily moved and adjusted, whereby it is possible to move and adjust the position of the cell sample S under observation on the slide glass 21 in the orthogonal direction to the optical axis of a microscope objective lens 61 facing the center opening in the sample table 1.

The total internal reflection sample illuminator used with the microscopic cell observation and inspection system of the invention—explained with reference to the aforesaid example—is common to the prior art multiple total internal reflection type shown in FIGS. 15(*a*) and 15(*b*) in that the laser light is subjected to multiple total internal reflections within the slide glass 21. If a slide glass thicker than an ordinary thickness of 0.17 to 0.2 mm is used as the slide glass 21, however, it is then possible to minimize the number of times of multiple total internal reflections, thereby preventing a drop of SN ratios upon fluorescent observation. In the aforesaid example, the number of times of multiple total internal reflections on the upper surface of the slide glass 21 with the sample S placed on it is four: there are four discrete areas illuminated with evanescent waves Ev, as shown in FIG. 2.

It is also possible to optimize the position of the radiation prism 4 thereby preventing scattered light from resulting from the laser light 10 that leaves the slide glass 21 after multiple total internal reflections.

And the sample is easily manipulated from above, and combined use with other optical observation methods and low-magnification observation at high SN ratios are viable as well. The sample container used may be a slide glass chamber for cell culture such as the aforesaid one, and there is no need of processing slide glasses at all, leading to improved versatility.

Further, the observation position on the slide glass 21 is changeable arbitrarily, freely and fast via the position adjustment mechanism at the X-Y stage 50, so that a lot of cell samples S positioned within the plane of the slide glass 21 can be observed in a fast switchover way.

It is here noted that when there is a change in the thickness of the slide glass 21, there is also a change in the reflection position on the upper surface of the slide glass 21. Consequently, the area illuminated with the evanescent waves Ev is off the optical axis of the microscope objective lens 61. Therefore, to implement observation when there is a change in the thickness of the slide glass 21, any of the sample table 1, objective lens 61 and reflecting mirror 12 is moved and adjusted in the X-direction in association with a shift of the position irradiated with the evanescent waves Ev.

Now then, the invention uses the total internal reflection sample illuminator of such structure as mentioned above to implement observation of the same cell sample S on the slide glass 21 under a TIRF microscope, a drop fluorescence microscope or a confocal fluorescence microscope in a fast switchover way.

Figure 3:
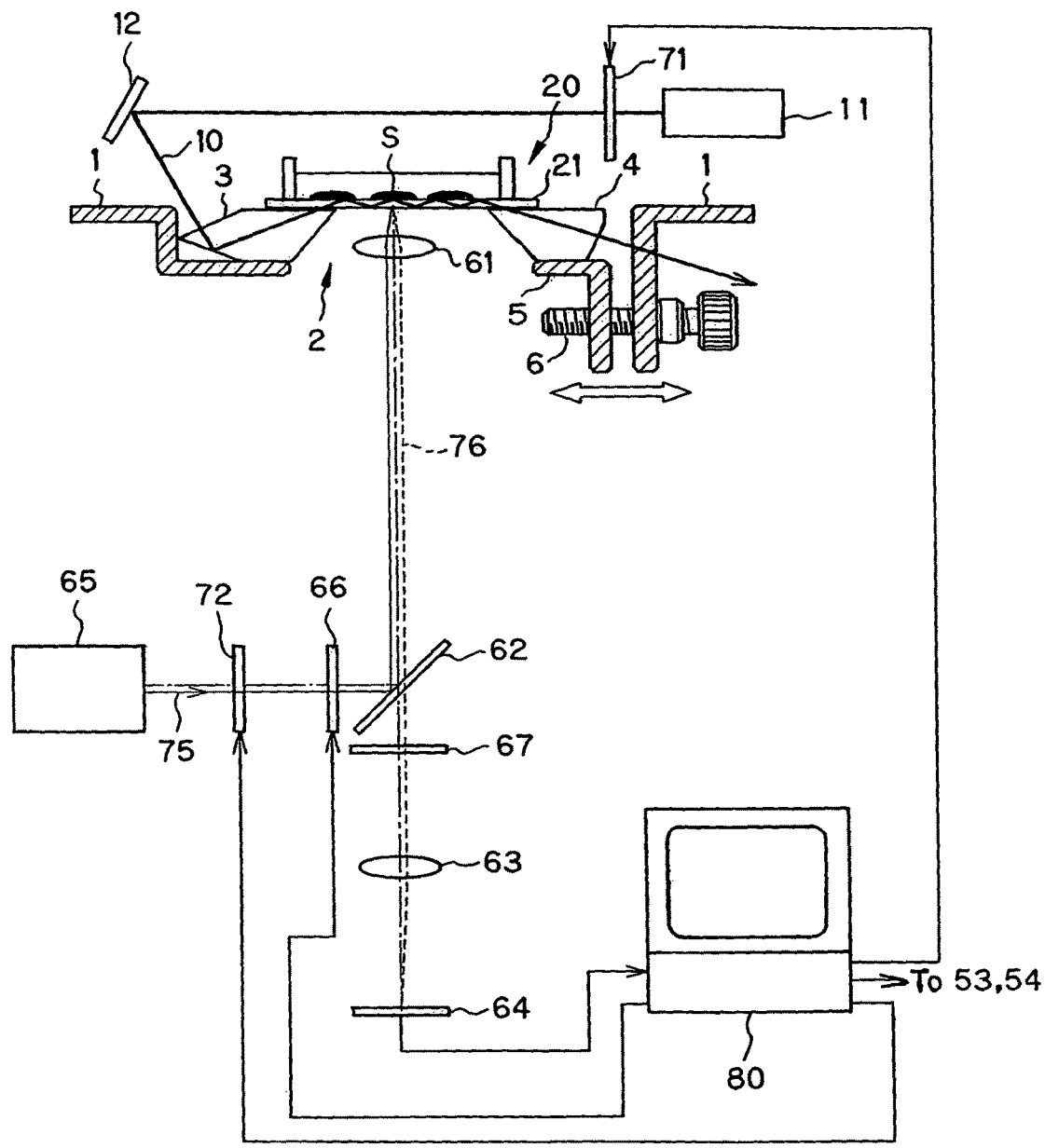
FIG. 3 is illustrative of the construction of one example of the invention, wherein the microscopic cell observation and inspection system can be used in combination with observations under a TIRF microscope and a drop fluorescence microscope.

FIG. 3 is illustrative of one example of that, i.e., the construction of the microscopic cell observation and inspection system that can be used in combination with observations under the TIRF microscope and drop fluorescence microscope. That construction is now explained.

There is an opening 2 formed in the center of the sample table 1 of FIGS. 1 and 2, under which there is a microscope objective lens 61 of the inverted type located, and there is a dichroic mirror 62 located obliquely located in an optical path through that microscope objective lens 61 on the observation side. And there is an imaging lens 63 located in an optical path of light transmitting through the dichroic mirror 62, and an imaging device 64 such as a CCD is located in the imaging plane.

On the other hand, a drop fluorescent illumination light source 65 such as a xenon lamp is located on the incidence side of the obliquely disposed dichroic mirror 62. And between the drop fluorescence illumination light source 65 and the dichroic mirror 62 there is an excitation wavelength select filter unit 66 located.

Further, a shutter unit 71 for blocking off or transmitting laser light 10 is disposed in an optical path between the entrance prism 3 and the evanescent wave-generation laser light 11 in the total internal reflection sample illuminator of FIGS. 1 and 2, and between the drop fluorescence illumination light source 65 and the dichroic mirror 62 there is a shutter unit 72 for blocking off or transmitting drop fluorescence excitation light.

Between the dichroic mirror 62 and the imaging lens 63, there is a barrier filter 62 for blocking off fluorescence of unwanted wavelengths, etc.

And the aforesaid shutter units 71, 72, filter unit 66, and step motors 53, 54 (FIG. 2) for moving and adjusting the observation position of the cell sample S on the slide glass 21 are connected to a personal computer 80, and switchover or positions of them are controlled by a command from the personal computer 80. Fluorescent images of the cell sample S taken by the imaging device 64 based on such operations are captured in the personal computer 80 for given image processing.

The microscopic cell observation and inspection system of FIG. 3 being arranged like such, while the step motors 53, 54 are driven in response to a command from the personal computer 80 to sequentially scan the observation positions of the cell sample S on the slide glass 21, one of the shutter units 71 and 72 is closed and another opened at high speed, whereby either one of the optical paths through the TIRF microscope and drop fluorescence microscope is selected to illuminate the cell sample S on that observation position. When the drop fluorescence microscope is chosen, the filter unit 66 is driven to choose the wavelength of excitation light from the drop fluorescent illumination light source 65, whereby the observation and inspection of the cell sample S under the TIRF microscope and drop fluorescence microscope can be implemented in a fast switchover way.

In addition, the total internal reflection sample illuminator used with the microscopic cell observation and inspection system of the invention can make use of a generally available slide glass chamber or slide glass without recourse to any special ones, and change the cell sample S to be observed and inspected on the slide glass chamber 20 or slide glass 21 to an arbitrary position at a fast speed without any movement of the light source laser 11 or microscope objective lens 61; for instance, if a chemical is added to the cell sample S on the slide glass 21 in a varying concentration or kind depending on position, it is then possible to make sure rapid detection of the efficacy of the chemical, etc. on the same cultured cell.

Examples of detection using the microscopic cell observation and inspection system of FIG. 3 are now explained.

Figure 4:
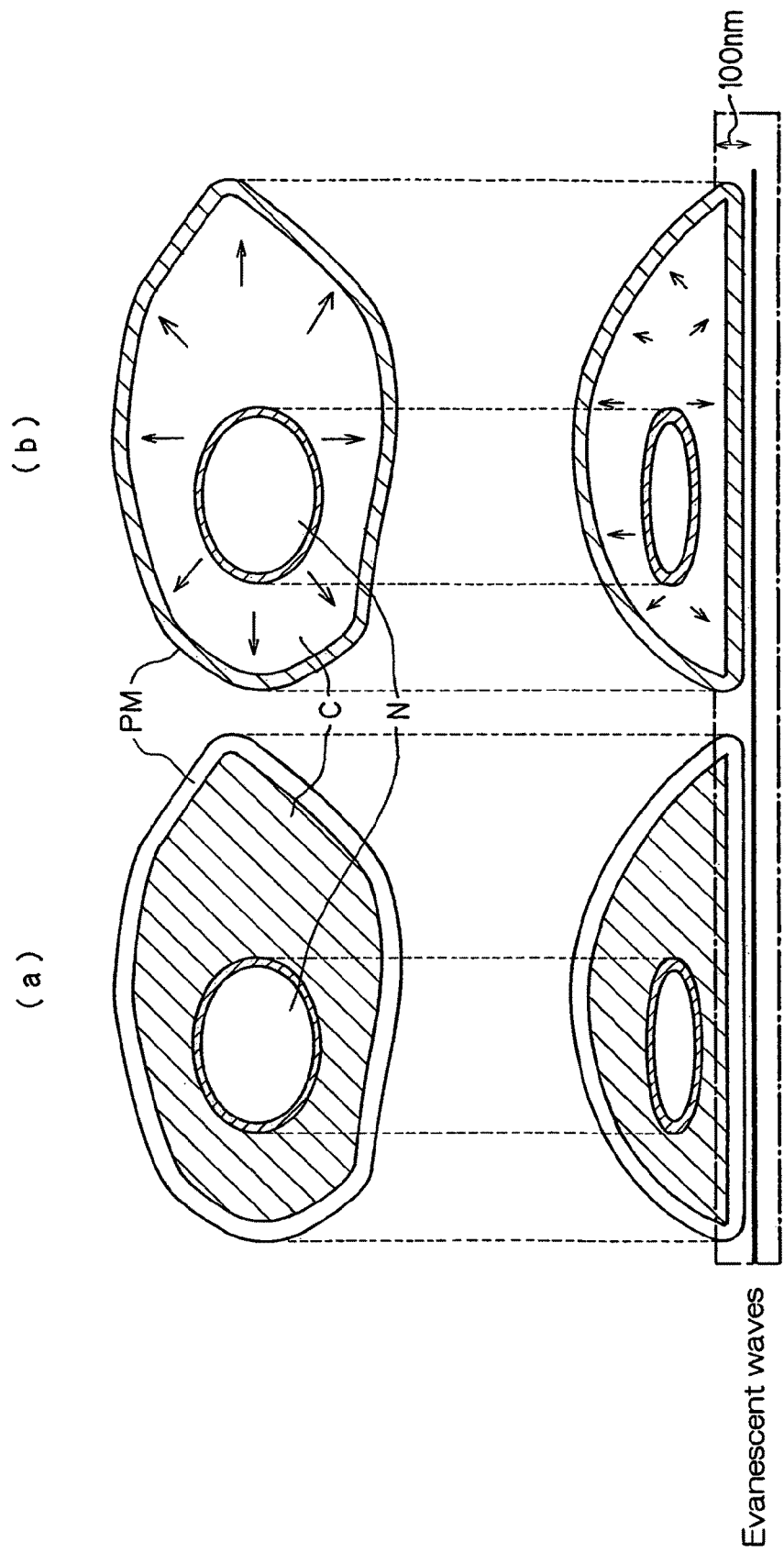
FIG. 4 is illustrative in schematic of results observed under drop fluorescence illumination, with a fused protein kinase Cα and green fluorescent protein combination genetically introduced into a cell.

FIG. 4 is illustrative in schematic of results of observation under drop fluorescent illumination of a cell with the genetic introduction in it of a fused protein of protein kinase Cα (PKCα) that is one of polyfunctional enzymes and green fluorescent protein (GFP). As shown in FIGS. 4(a) and 4(b), PKCα localizes from within cytoplasm C to a cell membrane PM upon receipt of depolarization stimulation, at which it is activated. Arrows directing from the nucleus N of FIG. 4(b) toward radiation directions are the directions of localization of PKCα, and hatched portions of FIG. 4 are indicative of sites where the concentration of PKCα is high. In FIGS. 4(a) and 4(b), the upper is a plan view and the lower a side view. With a change of this localization as an index to PKC activation, PKC activation could be monitored over time as a change in the spatial fluorescence intensity of GFP in a living cell.

The aforesaid phenomenon is two-dimensionally observed under a drop fluorescence microscope in the form of migration of green fluorescence from the upper drawing of FIG. 4(a) to the upper drawing of FIG. 4(b). Fluorescence intensity changes are viewed in the form of changes in the opposite directions: a decrease in the intensity of green fluorescence at the cytoplasm C and an increase in the intensity of green fluorescence at the cell membrane PM.

Under a TIRF microscope, by contrast, the same phenomenon is viewed in the form of migration of green fluorescence from the lower drawing of FIG. 4(a) to the lower drawing of FIG. 4(b): in the form of an exponential increase in the intensity of fluorescence of GFP near the lower cell membrane PF of the cell (the range of about 100 nm from the glass surface at which the evanescent field occurs), which leads to much more improved SN ratios.

Figure 5:
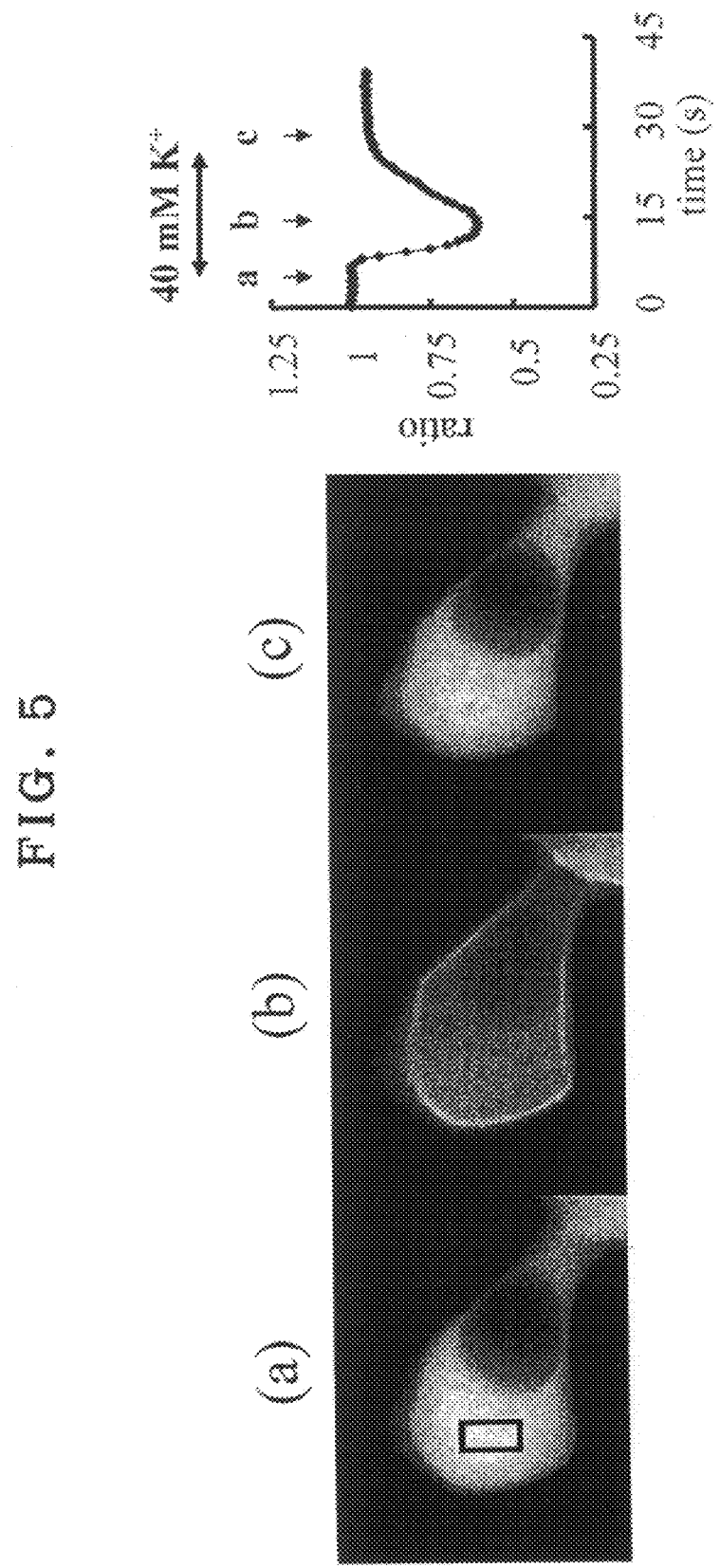
FIG. 5 is illustrative of one example of experimentation about changes in the drop fluorescence microscope image, corresponding to the upper and lower drawings of FIG. 4.

FIGS. 5 and 6 are indicative of changes in images viewed under the drop fluorescence microscope and TIRF microscope, respectively, corresponding to the upper and lower drawings of FIG. 4. More specifically, FIGS. 5(a), 5(b) and 5(c) and FIGS. 6(a), 6(b) and 6(c) are views illustrative of experimental examples with the introduction in living cells of ions $K^+$ for depolarization stimulation. A graph at the right side of FIG. 5, and FIG. 6 is indicative of changes in the intensity of fluorescence in the area of interest (the rectangular area in (a)), referring to the same phenomenon. However, it is found that there is an about ten-fold difference in the amount of change depending on the difference in the measuring methods (detections under the drop fluorescence microscope and TIRF microscope).

Figure 7:
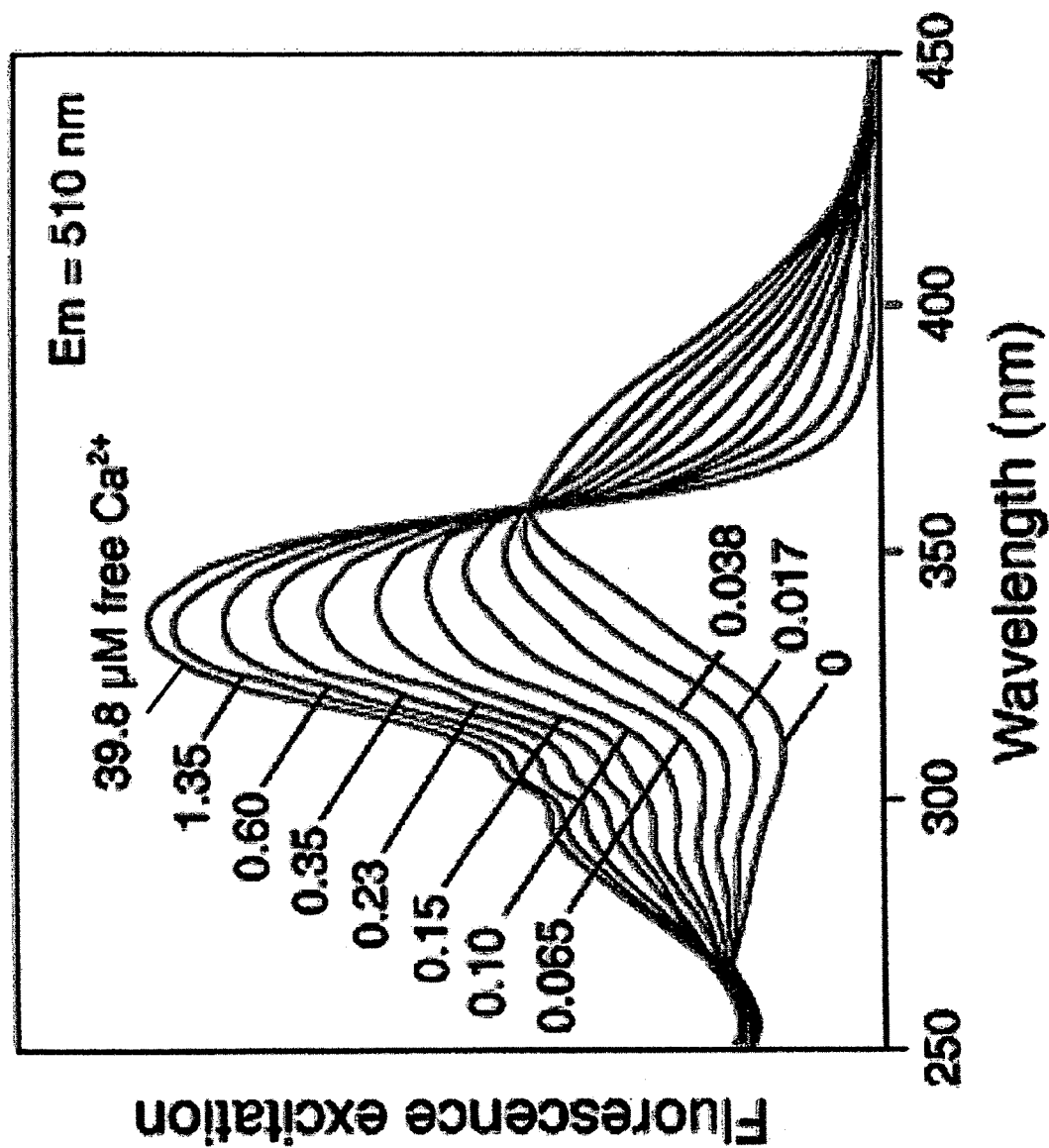
FIG. 7 is illustrative of the calcium concentration of Fura 2 vs. fluorescent characteristics with respect to excitation wavelengths.

By the way, the concentration of calcium in a calcium sensitive dye Fura 2 is measured in the form of the ratio of change in the intensity value of fluorescence near 510 nm that is a fluorescence wavelength as Fura 2 is excited at two wavelengths of 340 nm and 380 nm. FIG. 7 is illustrative of the calcium concentration of Fura 2 vs. fluorescence characteristics with respect to excitation wavelengths. In FIG. 7, Em is a fluorescence wavelength. That is, as there is a rise in the concentration of calcium in a cell due to depolarization stimulation, there is a decrease in the 510 nm fluorescence wavelength of Fura 2 loaded into the cell excited at 380 nm, whereas there is rather an increase in the 510 nm fluorescence wavelength of Fura 2 excited at 340 nm. Therefore, as there is a rise in the concentration of calcium in the cell, there is an increase in the value of (510 nm fluorescence intensity of Fura 2 excited at 340 nm/510 nm fluorescence intensity of Fura 2 excited at 380 nm).

Figure 8:
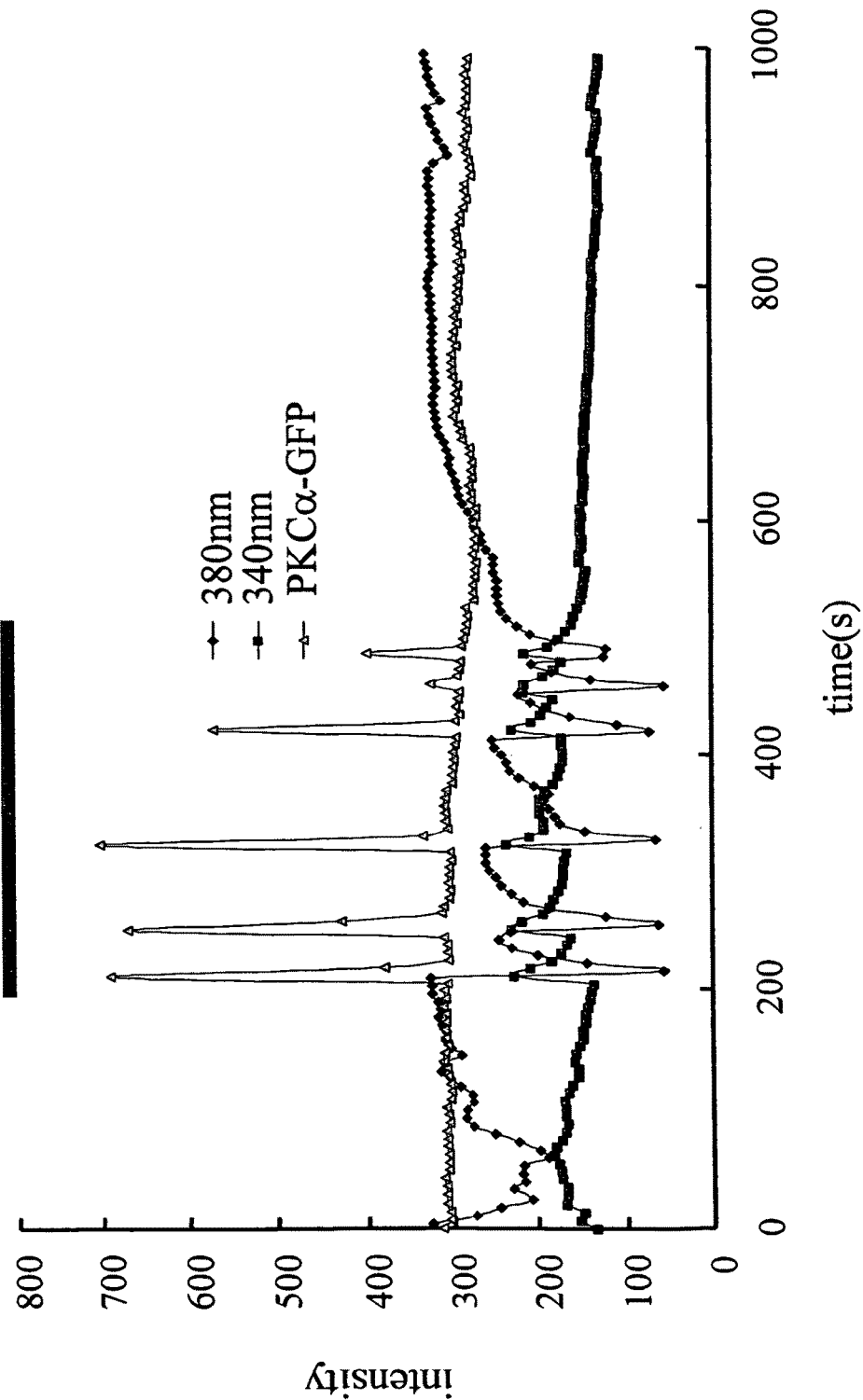
FIG. 8 is illustrative of fluorescence intensity changes of Fura 2 due to 2 ultraviolet excitation wavelengths measured using the drop fluorescence microscope of FIG. 3, and changes-over-time in the values of changes in the fluorescence intensity of GFR using the TIRF microscope of FIG. 3.

FIG. 8 is illustrative of changes over time of values found by alternate measurement at a one-second interval of changes in the fluorescence intensity of Fura 2 at two ultraviolet excitation wavelengths using the drop fluorescence microscope of FIG. 3, and changes in the fluorescence intensity of GFP using the TIRF microscope of FIG. 3. In FIG. 8, TEA is a chemical (tetraethyl-ammonium) added for the purpose of depolarization stimulation.

That is, in FIG. 3, the step motors 53, 54 are first driven in response to a command from the personal computer 80 to select a specific observation position for the cell sample S on the slide glass 21. Then, the shutter unit 71 is opened with the shutter unit 72 remaining closed to select the illumination optical path for the TIRF microscope. Then, the cell sample S at that observation position is illuminated with the evanescent wave Ev generated while the laser light 10 is subjected to multiple total internal reflections through the slide glass 21. Finally, a PKCα-GFP fluorescent image that is a fluorescent image of that sample is formed on the imaging device 64 by the imaging lens 63 via the microscope objective lens 61 and dichroic mirror 62, following by capturing the ensuing image in the personal computer 80.

Then, the shutter unit 71 is closed and the shutter unit 72 is opened and, at the same time, the filter unit 66 is driven to select 340 nm out of the wavelengths of excitation light 75 from the drop fluorescence illumination light source 65. Then, the cell sample S at that observation position is illuminated with that excitation light 75 via the microscope objective lens 61 in a drop illumination way. Finally, fluorescence 76 from that observation position is imaged on the imaging device 64 by the imaging lens 63 via the microscope objective lens 61 and dichroic mirror 62, followed by capturing a fluorescent image of 510 nm fluorescence wavelength excited with 340 nm excitation light in the personal computer 80.

Then, while this time the shutter unit 71 remains closed and the shutter unit 72 remains opened, the filter unit 66 is driven to select 380 nm of the excitation light 75 from the drop fluorescence illumination light source 65 so that the cell sample S at that observation position is illuminated with the excitation light 75 via the microscope objective lens 61 in a drop illumination way. Finally, fluorescence 76 from that observation position is imaged on the imaging device 64 by the imaging lens 63 via the microscope objective lens 61 and dichroic mirror 62, followed by capturing a fluorescent image of 510 nm fluorescence wavelength excited with 340 nm excitation light in the personal computer 80.

This process is repeated for a specific observation position whereby there is such a change over time as shown in FIG. 8 obtained.

By measuring the behaviors of quite different parameters (polyfunctional enzyme and calcium concentration), it is thus possible to enhance the sensitivity and specificity of the cell to reactions. Referring again to FIG. 8, it is noted that as the calcium concentration rises, there is a change in the localization of PKCα. However, it is not that the increase in the calcium concentration necessarily leads to the change in the localization of PKCα: the aforesaid phenomenon is going to occur depending on cell states, the concentration and type of the chemical added, etc.

Figure 9:
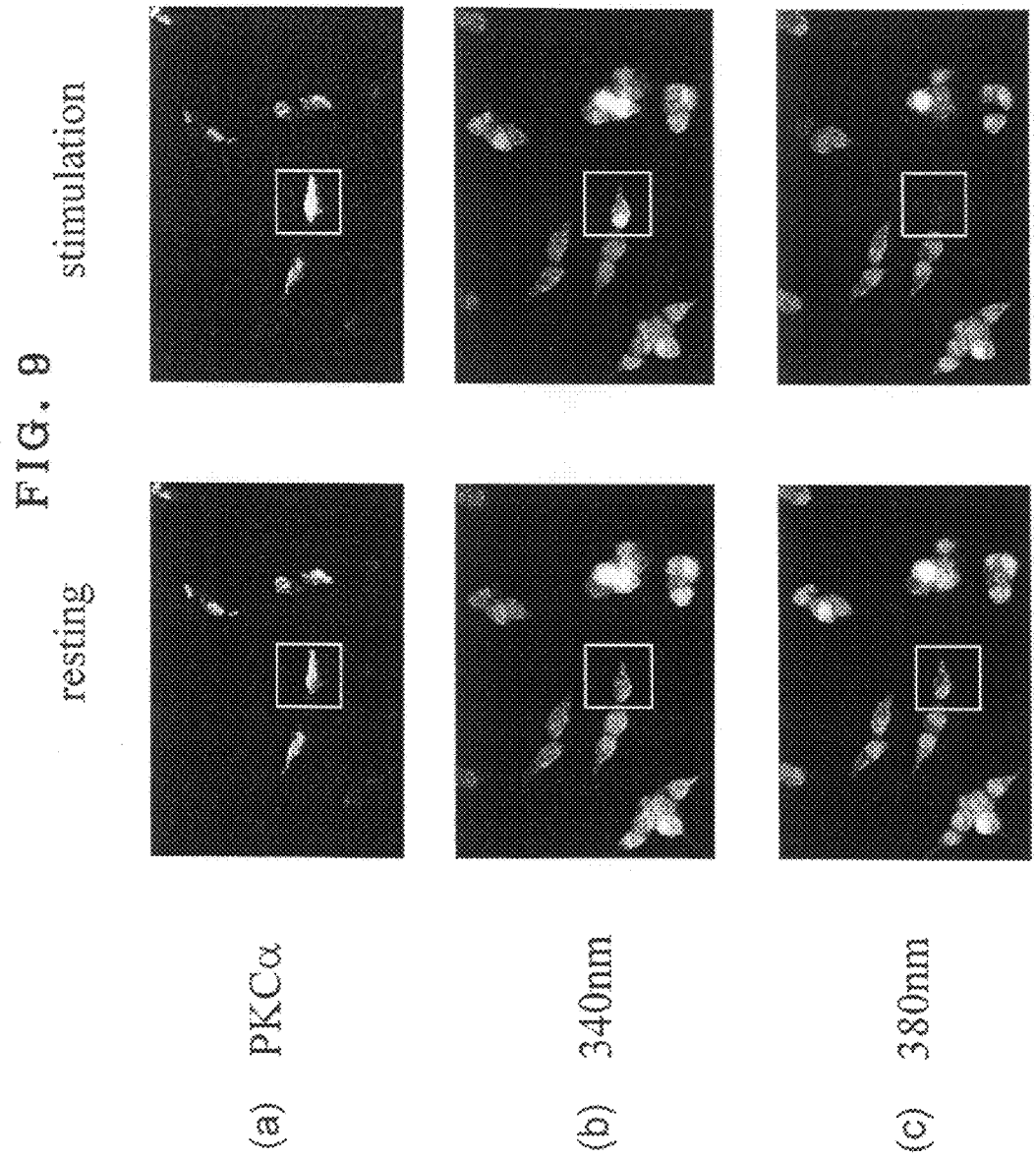
FIG. 9 is illustrative of changes in the TIRF microscope image (a) corresponding to FIG. 8, a drop fluorescence microscope image (b) at an excitation wavelength of 340 nm, and a drop fluorescence microscope image (c) at an excitation wavelength of 380 nm.

FIGS. 9(*a*), 9(*b*) and 9(*c*), corresponding to FIG. 8, are illustrative of changes in images under the TIRF microscope (a), the drop fluorescence microscope at 340 nm excitation wavelength (b), and the drop fluorescence microscope at 380 nm excitation wavelength, with the left being images before depolarization stimulation (resting) and the right being images upon depolarization stimulation (stimulation). Changes in the rectangles are found to be in coincidence with those in the foregoing explanation.

Figure 10:
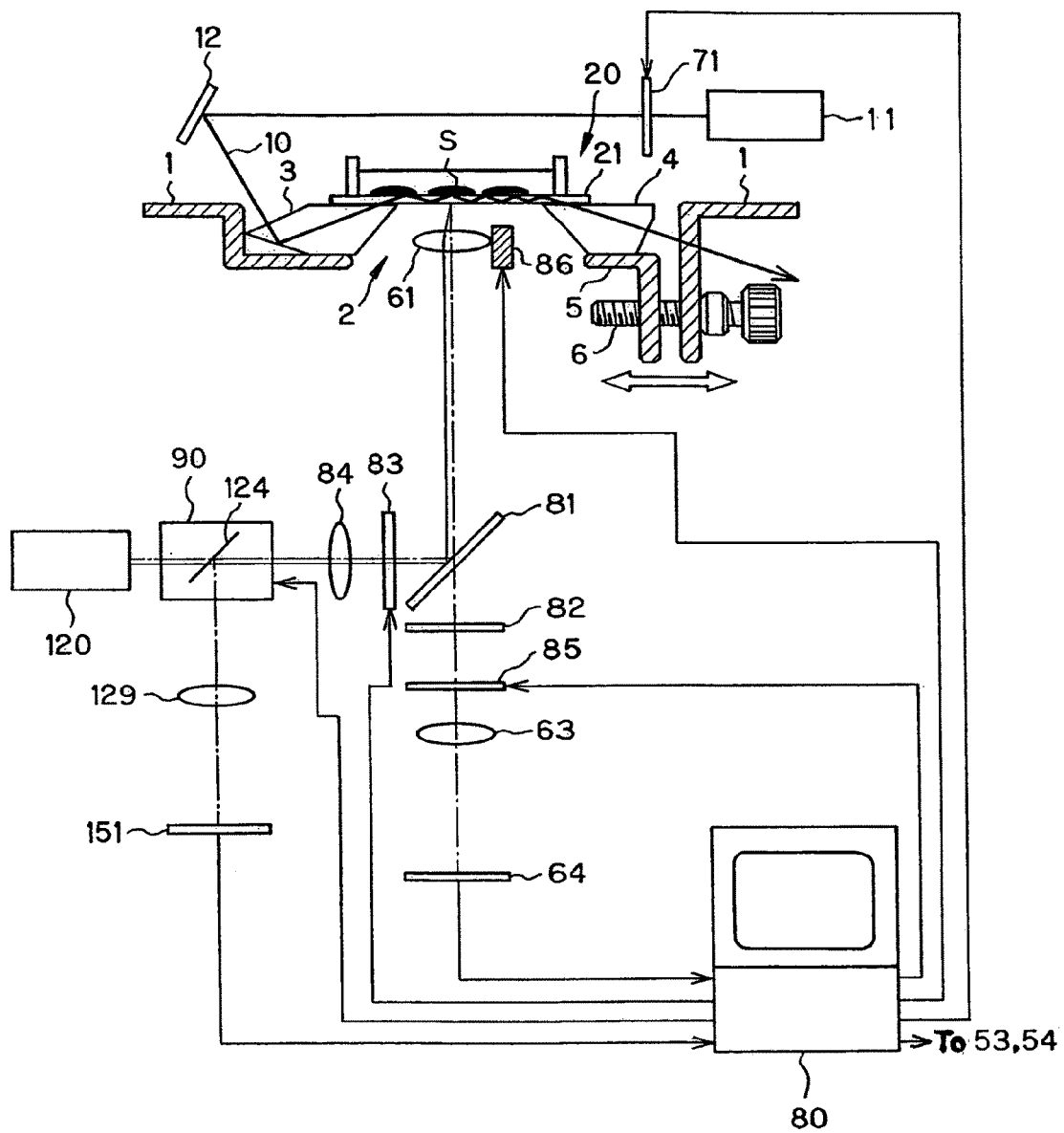
FIG. 10 is illustrative of the construction of another example of the invention, wherein the microscopic cell observation and inspection system can be used in combination with observations under a TIRF microscope and a confocal fluorescence microscope.

Referring then to FIG. 10, it is illustrative of the construction of another example of the microscopic cell observation and inspection system that may be used in combination with observations under a TIRF microscope and a confocal fluorescence microscope. The arrangement here is now explained.

As is the case with the example of FIG. 3, the opening 2 is provided in the center of the sample table 1, and below that there is a microscope objective lens 61 of the inverted type located. A half-mirror 81 is obliquely located in an optical path on the objection side of that microscope objective lens 61. And an excitation light cut filter 82, a shutter unit 85 and an imaging lens 63 are located in a path taken by light transmitting through the half-mirror 81, and an imaging device 64 such as a CCD is located on the imaging plane of that imaging lens 63.

On the reflection side of the obliquely located half-mirror 8, on the other hand, there are a Nipkow type confocal scanner 90 and a laser 120 for illuminating it located via a relay lens 84, and on the output side of the confocal scanner 90 there is an imaging lens 129 located, with an imaging device 151 such as a CCD located on the imaging plane of that imaging lens.

The microscope objective lens 61 here is adjustable by a piezo element 86 in terms of position in the optical axis direction.

Further, in an optical path between the entrance prism 3 and the laser 11 for generating the evanescent wave-generation laser light 10 in the total internal reflection sample illuminator of FIGS. 1 and 2, there is a shutter unit 71 provided for blocking off or transmitting the laser light 10, and between the confocal scanner 90 and the half-mirror 81, there is a shutter unit 83 located for blocking off or transmitting confocal scan light.

Here, when the shutter unit 83 stays open, the laser light or excitation light generated from the laser 120 passes through the Nipkow type confocal scanner 90 and relay lens 84, turning into parallel scan light, which is in turn reflected off at the half-mirror 81. The reflected light then converges onto a given object surface in the cell sample S on the slide glass 21 via the microscope objective lens 61. Fluorescence emitted out of the cell sample S excited by the laser light comes back to the confocal scanner 90 via the microscope objective lens 61, half-mirror 81 and relay lens 84, and is reflected off at a dichroic mirror 124 in the cofoncal scanner 90, imaging an fluorescent image of the given object surface in the cell sample S on an imaging device 151 through an imaging lens 129.

Figure 11:
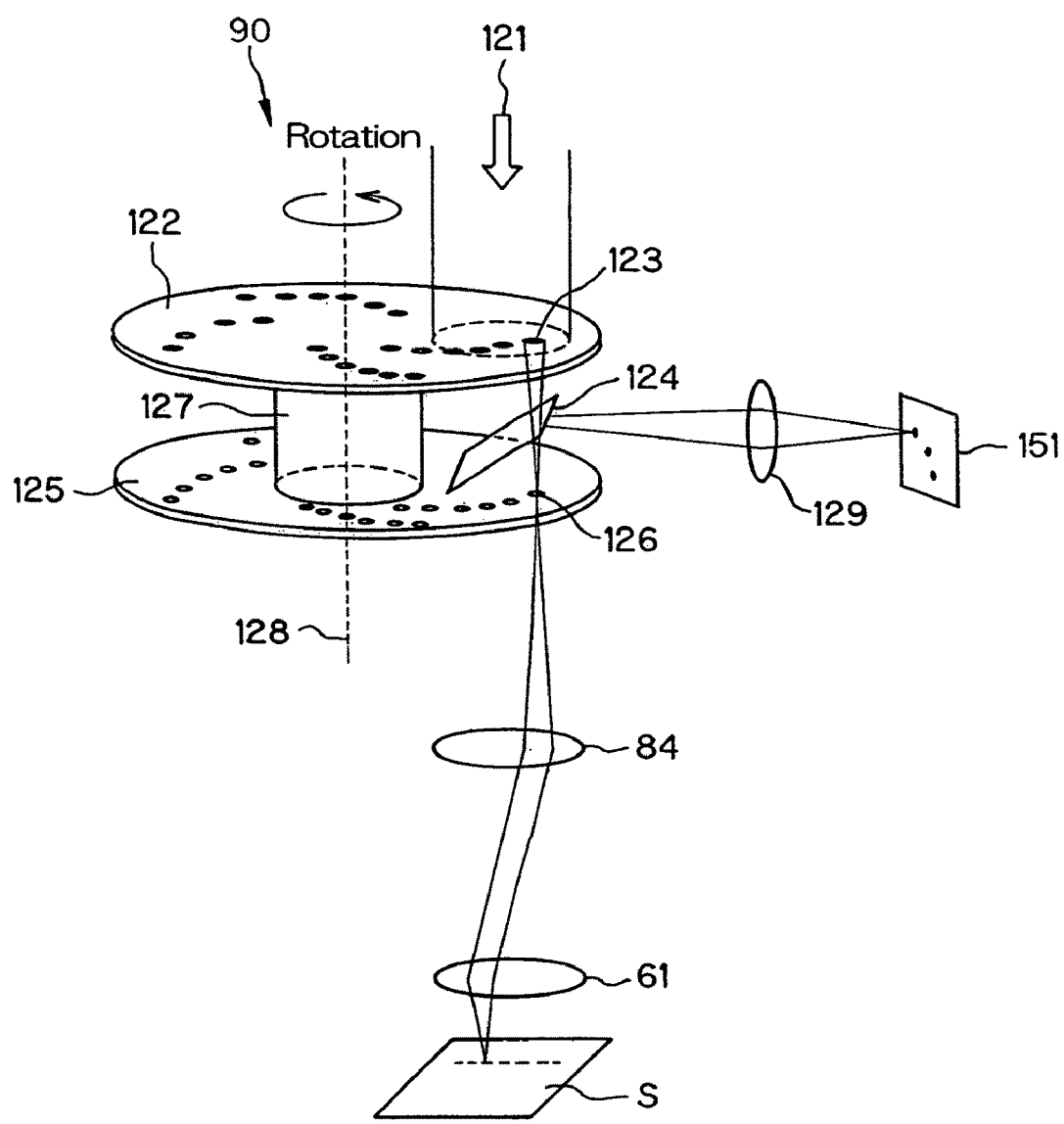
FIG. 11 is illustrative of the construction of a Nipkow type confocal scanner.

The Nipkow type confocal scanner 90, for instance, has such construction as shown in FIG. 11. In FIG. 11, laser light 121 or excitation light from a laser 120 is converged into individual light beams by means of individual microlens 123 located on a microlens disk 122, and after transmitting through the dichroic mirror 124, those light beams pass through individual pinholes 126 formed in a pinhole disk (also called the Nipkow disk) 125, coming together at the given object surface in the cell sample S via the relay lens 84 and microscope objective lens 61.

Fluorescence given out of the cell sample S again passes through the microscope objective lens 61, half-mirror 81 (FIG. 10) and relay lens 84, coming together on the individual pinholes 126 in the pinhole disk 125. Fluorescence transmitting through the individual pinholes 126 is reflected off at the dichroic mirror 124, imaging a fluorescent image on the imaging device 151 such as CCD in the imaging unit by means of the imaging lens 129.

The dichroic mirror 124 used here is designed in such a way as to transmit excitation light 121 and reflect fluorescence from the cell sample S.

The microlens disk 122 is mechanically coupled by a member 127 to the pinhole disk 125 so that they rotate around a rotary shaft 128. The individual microlenses 123 and pinholes 126 are located such that the plane of the cell sample S under observation is scanned by excitation light from the individual pinholes 126 formed in the pinhole disk 125. The plane with the pinholes 126 lined up on it, the plane of the cell sample S under observation and the imaging device 151 in the imaging unit are located in mutually optically conjugate relations so that optical section images, viz., confocal images of the cell sample S are formed on the imaging device 151.

And the foregoing shutter units 71, 83, 85, Nipkow type confocal scanner 90, piezo element 86 for adjusting the position of the object plane (plane under observation) of the microscope objective lens 61 relative to the cell sample S, and step motors 53, 54 (FIG. 2) for moving and adjusting the observation position of the cell sample S on the slide glass 21 are connected to the personal computer 80, and their switchover or position control is implemented in response to a command from the personal computer 80. Fluorescent images of the cell sample S taken by the imaging device 64, 151 based on their operations are captured in the personal computer 80 for the purpose of implementing the necessary imaging processing.

The microscopic cell observation and inspection system of FIG. 10 being constructed like such, the step motors 53, 54 are driven in response to a command from the personal computer 80 to sequentially scan the observation positions of the cell sample S on the slide glass 21. In the meantime, one of the shutter units 71 and 82 and the shutter unit 83 is fast closed and another is opened, whereby one of the observation optical paths through the TIRF and confocal fluorescence microscopes is selected to illuminate the cell sample S at the position under observation. When the confocal fluorescence microscope is chosen, the piezo element 86 is controlled to adjust the position of the microscope objective lens 61 in the optical axis direction at a video rate so that confocal planes are varied by a predetermined number to take a florescent image of each cell section by the imaging device 151. Finally, the fluorescent image of each section is captured in the personal computer 80 to construct a three-dimensional fluorescent image of the cell sample S.

When there is the observation optical path for the TIRF microscope chosen, the cell sample S at that observation position is illuminated with evanescent waves Ev generated while the laser light 10 is subjected to multiple total internal reflections in the slide glass 21, and the ensuing fluorescent image is imaged by the imaging lens 63 and taken by the imaging device 64 via the microscope objective lens 61, half-mirror 81 and excitation light cut filter 82, and then captured in the personal computer 80.

In this way, for instance, each section in the cell is imaged by the confocal fluorescence microscope and sites near the cell membrane are imaged by the TIRF microscope so that the behaviors of a protein mass migrating in cell organelles and cytoplasm and between cell membranes can be viewed using fluorescent protein.

In the examples described above, the excitation light source or the lasers 11, 120 are supposed to have a single wavelength, and the fluorescence wavelength is supposed to be a single one as well. However, it is understood that a laser combiner may be used to superpose a plurality of excitation wavelengths one upon another over time or at the same time or, alternatively, to take fluorescent images having different wavelengths corresponding to the respective excitation wavelengths, a fluorescence separation unit may be disposed in front of a CCD camera (imaging lens 63 plus imaging device 64, or imaging lens 129 plus imaging device 151) or a color CCD camera may be used to take a multicolor image.

An example of detection using the microscopic cell observation and inspection system of FIG. 10 is now explained: a plurality of fluorescence wavelength images can be simultaneously taken.

Figure 12:
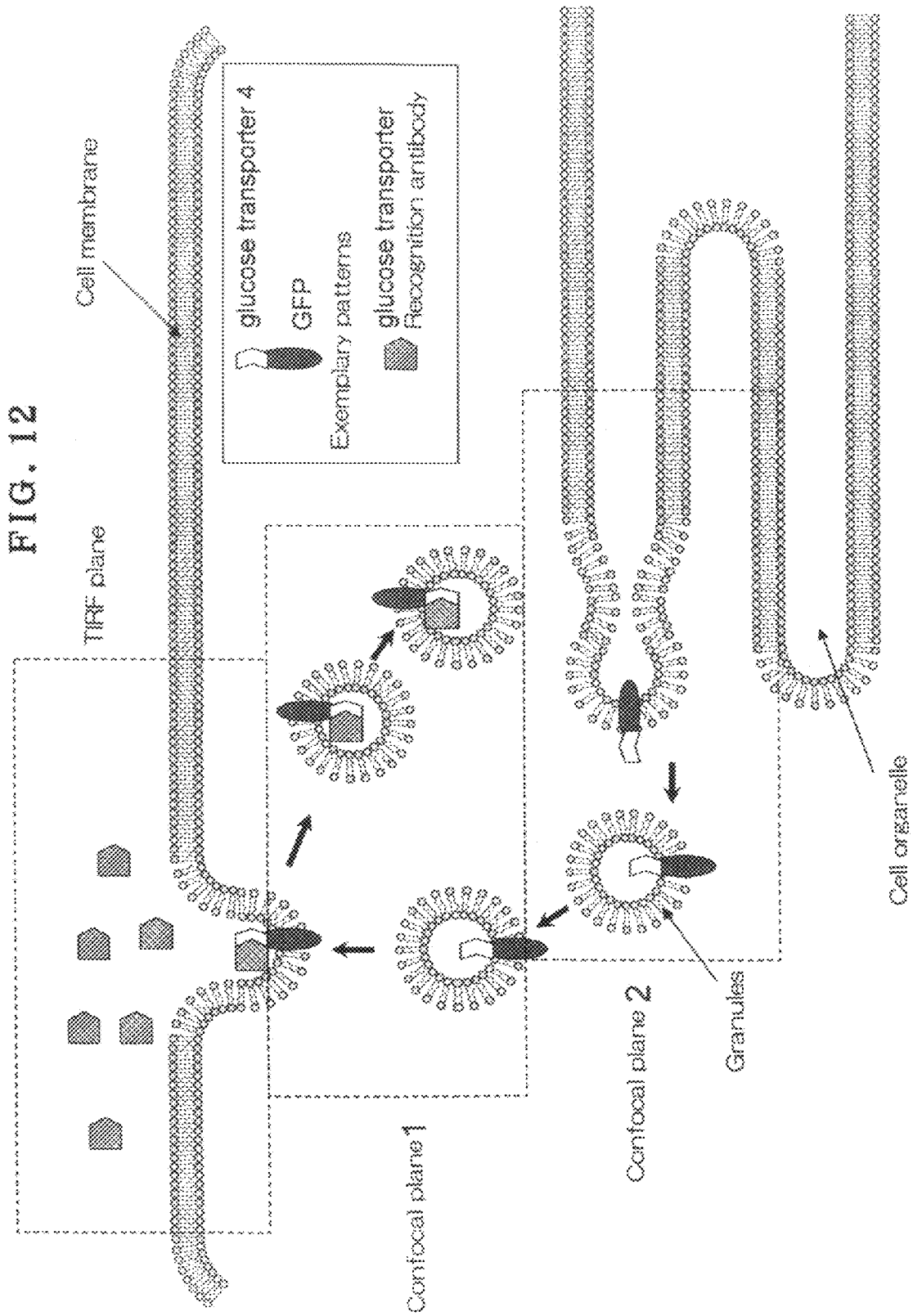
FIG. 12 is illustrative in schematic of the behavior of a glucose transporter.
Figure 13:
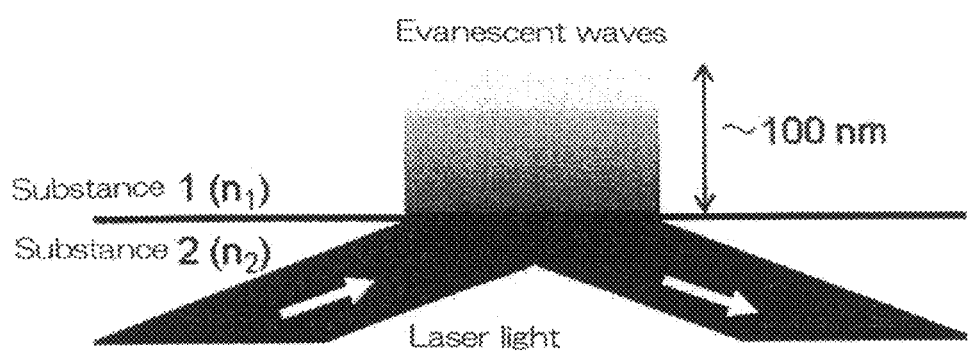
FIG. 13 is illustrative of how evanescent waves are generated with the TIRF microscope technique.

FIG. 12 is illustrative in schematic of the behavior of a glucose transporter. The glucose transporter works as a sort of a device of taking sugar in an in-vivo cell. In a muscle or fat, glucose transporter 4 (Glut 4) is incorporated in its cell and, as shown in FIG. 12, and it is delivered by granules from the Golgi body of the cell organelle. As a lot of Glut 4's are localized from within the cell to the cell membrane via insulin stimulation, it permits the rate of taking sugar in to increase. Here, as shown in FIG. 12, a fused protein of Glut 4 and green fluorescent protein (GFP) is genetically introduced, a recognition antibody capable of recognizing that Glut 4 is previously labeled with a red dye (alexa 568 or the like), and a glucose transporter recognition antibody is disposed outside the cell. As Glut 4 shows up on the cell membrane by insulin stimulation, the fluorescence intensity of GFP rises, and the recognition antibody labeled with the red dye is bonded to Glut 4: that Glut 4 has indeed been migrated onto the cell membrane is made certain under the TIRF microscope. With that, how Glue 4 returns again within the cell is also observable under the confocal fluorescence microscope. Where Glut 4 goes out is comparable with where Glut 4 goes back to. In that case, at the TIRF plane with evanescent waves existing on it, the bond of Glut 4 with the recognition antibody can be confirmed and observed. Further, the behavior of Glut 4 migrating onto the cell membrane can be observed under the confocal fluorescence microscope, and the behavior of Glut 4 going back from the cell membrane is observed on, for instance, confocal planes 1 to 10 or the like. The apparatus of FIG. 10 is useful for the continuous taking of such fluorescent images.

It is noted that the apparatus of FIG. 3 may be combined with the apparatus of FIG. 10 (for instance, by locating the half-mirror 81 between the microscope objective lens 61 and the dichroic mirror 62 in FIG. 3) to enable combined use of observations under the TIRF microscope, drop fluorescence microscope and confocal fluorescence microscope.

With the aforesaid microscopic cell observation and inspection system of the invention using a plurality of observation ways, it is possible to observe and inspect nano-scale phenomena in association with a plurality of cells or bio-high molecules at low magnifications and at the same time. The system enables changes in the localization of organelles, protein delivery and protein in a lot of cells to be observed and inspected at the same time or almost simultaneously, so that morphological comparison, analysis of protein delivery mechanism, and detection of enzyme activity can be facilitated, making a great contribution to studies in the cell biological field and drug design screening. Further, since commercial slide glass chambers for cell culture are used for sample containers, the inventive system is of by far greater versatility. Still further, since as many as several hundreds of cell reactions are detectable on the same slide glass with high sensitivity at high speed, the system of the invention may be used as a drug design screening system.

What we claim is:

1. A microscopic observation and inspection system using a plurality of observation methods, characterized by comprising a total internal reflection sample illuminator comprising an evanescent wave-generation light source in which laser light from that light source is introduced into a slide glass through which the laser light is guided by multiple total internal reflections to generate evanescent waves on an upper surface of said slide glass so that a cell sample placed on the upper surface of said slide glass is illuminated with said evanescent waves, wherein:

said total internal reflection sample illuminator comprises an entrance prism and a radiation prism which support said slide glass movably in a plane thereof via a droplet of index-matching liquid, said entrance prism is fixed with respect to said evanescent wave-generation light source, and said radiation prism is located in such a way as to be adjustable in terms of position in a direction of travel of said laser light with respect to said entrance prism, a supporting surface of said entrance prism for said slide glass is flush with a supporting surface of said radiation prism for said slide glass irrespective of a position of the said radiation prism being adjusted, there is a slide glass position adjustment mechanism provided which takes a grip on said slide glass supported on said entrance prism and said radiation prism to adjust a position of said slide glass in a two-dimensional direction along a plane thereof, said total internal reflection sample illuminator is set up such that said laser light leaves said supporting surface via said entrance prism and enters said slide glass supported thereon via said index-matching liquid trickling down thereon through which said laser light is guided by multiple total internal reflection, entering from said supporting surface of said radiation prism into said radiation prism via said index-matching liquid trickling down on said supporting surface of said radiation prism, and is radiated out from said radiation prism, and in response to a command from said controller, said slide glass position adjustment mechanism is controlled to select an observation and inspection position for the cell sample on said slide glass a microscope objective lens is located at a position where said slide glass in said total internal reflection sample illuminator is supposed to be placed thereon and in a vertical direction to said slide glass, on an imaging side of said microscope objective lens, an imaging optical system and an imaging device are located in one optical path via an optical path splitter and an excitation light source for a drop fluorescence microscope is located in another optical path, shutter units adapted to block off or transmit illumination light are located, one in an optical path from said evanescent wave-generation light source to a laser light inlet of said slide glass, and another between said excitation light source for a drop fluorescence microscope and said optical path splitter, there is a controller provided which controls an illumination light source switchover by opening or closing each of said shutter units and slide glass position adjustment by said slide glass position adjustment mechanism, and in response to a command from said controller, the opening or closing of each of said shutter units is controlled so that an illumination light optical path for said evanescent wave-generation light source and an illumination light optical path for said excitation light source for a drop fluorescence microscope are selectively opened, a total internal reflection fluorescence microscope image and a drop fluorescence microscope image at the selected cell sample observation and inspection site on said slide glass are captured in said controller via said imaging device, and cell reactions are detected from said total internal reflection fluorescence microscope image and said drop fluorescence microscope image.

2. The microscopic observation and inspection system using a plurality of observation methods according to claim 1, characterized in that said optical path splitter comprises a dichroic mirror and is operable to prevent light having a wavelength of illumination light from said evanescent wave-generation light source and light having a wavelength of illumination light from said excitation light source for a drop fluorescence microscope from arriving at said optical path on the imaging device side but allow only fluorescence emanating from the cell sample to arrive at said optical path on the imaging device side.

3. The microscopic observation and inspection system using a plurality of observation methods according to claim 2, characterized in that between said excitation light source for a drop fluorescence microscope and said optical path splitter there is a filter unit located which selects an excitation wavelength, and in response to a command from said controller an excitation wavelength transmitting through said filter unit is selected.

4. The microscopic observation and inspection system using a plurality of observation methods according to claim 1, characterized in that between said excitation light source for a drop fluorescence microscope and said optical path splitter there is a filter unit located which selects an excitation wavelength, and in response to a command from said controller an excitation wavelength transmitting through said filter unit is selected.

5. A microscopic observation and inspection system using a plurality of observation methods, characterized by comprising a total internal reflection sample illuminator comprising an evanescent wave-generation light source in which laser light from that light source is introduced into a slide glass through which the laser light is guided by multiple total internal reflections to generate evanescent waves on an upper surface of said slide glass so that a cell sample placed on the upper surface of said slide glass is illuminated with said evanescent waves, wherein:

a microscope objective lens is located at a position where said slide glass in said total internal reflection sample illuminator is supposed to be placed thereon and in a vertical direction to said slide glass, on an imaging side of said microscope objective lens, a filter for blocking off light having a wavelength of illumination light from said evanescent wave-generation light source, a first imaging optical system and a first imaging device are located in one optical path via an optical path splitter, and a confocal scanner for a confocal fluorescence microscope is located in another optical path, on an illumination side of said confocal scanner an excitation light source for the confocal fluorescence microscope is located, and on an output side of said confocal scanner a second imaging system and a second imaging device are located, shutter units adapted to block off or transmit illumination light or fluorescent light are located, one in an optical path from said evanescent wave-generation light source to a laser light inlet of said slide glass, another in an optical path between said confocal scanner and said optical path splitter, and yet another in an optical path between said optical path splitter and said first imaging device, there is a controller provided which controls an illumination light source switchover by opening or closing each of said shutter units, and a focus adjustment mechanism adapted to adjust a position of said microscope objective lens in an optical axis direction, and in response to a command from said controller, the opening or closing of each of said shutter units is controlled so that an illumination light optical path for said evanescent wave-generation light source and an illumination light optical path for a confocal scanner for said drop fluorescence microscope are selectively opened, and when the illumination optical path for the confocal scanner for said confocal fluorescence microscope is opened, said focus adjustment mechanism is controlled to adjust a position of said microscope objective lens in an optical axis direction to a plurality of given positions, whereby a total internal reflection fluorescence microscope image and a confocal fluorescence microscope image at the selected cell sample observation and inspection position on said slide glass are captured in said controller vial said first imaging device and said second imaging device, respectively, so that cell reactions are detected from said total internal reflection fluorescence microscope image and said confocal fluorescence microscope image.

6. The microscopic observation and inspection system using a plurality of observation methods according to claim 5, characterized in that:

said total internal reflection sample illuminator comprises an entrance prism and a radiation prism which support said slide glass movably in a plane thereof via a droplet of index-matching liquid, said entrance prism is fixed with respect to said light source, and said radiation prism is located in such a way as to be adjustable in terms of position in a direction of travel of said laser light with respect to said entrance prism, a supporting surface of said entrance prism for said slide glass is flush with a supporting surface of said radiation prism for said slide glass irrespective of a position of the said radiation prism being adjusted, there is a slide glass position adjustment mechanism provided which takes a grip on said slide glass supported on said entrance prism and said radiation prism to adjust a position of said slide glass in a two-dimensional direction along a plane thereof, said total internal reflection sample illuminator is set up such that said laser light leaves said supporting surface via said entrance prism and enters said slide glass supported thereon via said index-matching liquid trickling down thereon through which said laser light is guided by multiple total internal reflection, entering from said supporting surface of said radiation prism into said radiation prism via said index-matching liquid trickling down on said supporting surface of said radiation prism, and is radiated from said radiation prism toward outside, and in response to a command from said controller, said slide glass position adjustment mechanism is controlled to select an observation and inspection position for the cell sample on said slide glass.

\* \* \* \* \*